United States Patent
Khurana et al.

(10) Patent No.: US 11,867,672 B2
(45) Date of Patent: *Jan. 9, 2024

(54) FLOW CELL WITH ONE OR MORE BARRIER FEATURES

(71) Applicant: ILLUMINA, INC., San Diego, CA (US)

(72) Inventors: Tarun Khurana, Fremont, CA (US); Ali Agah, Menlo Park, CA (US); Aathavan Karunakaran, Berkeley, CA (US); Stanley Hong, Palo Alto, CA (US); Merek Siu, Alameda, CA (US); Arvin Emadi, San Jose, CA (US); Craig Ciesla, Mountain View, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,752

(22) Filed: Feb. 9, 2023

(65) Prior Publication Data
US 2023/0184725 A1    Jun. 15, 2023

Related U.S. Application Data

(63) Continuation of application No. 17/846,538, filed on Jun. 22, 2022, now Pat. No. 11,604,175, which is a
(Continued)

(51) Int. Cl.
*G01N 30/74* (2006.01)
*C12Q 1/6874* (2018.01)

(52) U.S. Cl.
CPC ........... *G01N 30/74* (2013.01); *C12Q 1/6874* (2013.01); *G01N 2030/746* (2013.01)

(58) Field of Classification Search
CPC .. G01N 30/74; G01N 2030/746; G01N 35/08; C12Q 1/6874; F16K 99/0013
(Continued)

(56) References Cited

U.S. PATENT DOCUMENTS

| | | | |
|---|---|---|---|
| 4,640,821 A | * | 2/1987 | Mody .................... G01N 35/08 436/52 |
| 5,314,825 A | | 5/1994 | Weyrauch et al. |

(Continued)

FOREIGN PATENT DOCUMENTS

| | | |
|---|---|---|
| EP | 2714935 B1 | 3/2017 |
| WO | WO 2003/035824 A1 | 5/2003 |

(Continued)

OTHER PUBLICATIONS

Extended European Search Report dated Dec. 12, 2022, for Application No. 20812857.9, 10 pages.
(Continued)

*Primary Examiner* — Isiaka O Akanbi
(74) *Attorney, Agent, or Firm* — FROST BROWN TODD LLP

(57) ABSTRACT

An apparatus includes a flow cell body, a plurality of electrodes, an imaging assembly, and one or more barrier features. The flow cell body defines one or more flow channels and a plurality of wells defined as recesses in the floor of each flow channel. Each well is fluidically coupled with the corresponding flow channel. The flow cell body further defines interstitial surfaces between adjacent wells. Each well defines a corresponding depth. Each electrode is positioned in a corresponding well of the plurality of wells. The electrodes are to effect writing of polynucleotides in the wells. The imaging assembly is to capture images of polynucleotides written in the wells. The one or more barrier features are positioned in the wells, between the wells, or
(Continued)

above the wells. The one or more barrier features contain reactions in each well, reduce diffusion between the wells, or reduce optical cross-talk between the wells.

13 Claims, 14 Drawing Sheets

Related U.S. Application Data continuation of application No. 17/479,342, filed on Sep. 20, 2021, now Pat. No. 11,402,358, which is a continuation of application No. 17/254,466, filed as application No. PCT/US2020/034518 on May 26, 2020, now Pat. No. 11,143,638.

(60) Provisional application No. 62/855,654, filed on May 31, 2019, provisional application No. 62/855,662, filed on May 31, 2019.

(58) Field of Classification Search
USPC ............... 356/246, 432–442, 240.1, 244
See application file for complete search history.

(56) References Cited

U.S. PATENT DOCUMENTS

| | | | |
|---|---|---|---|
| 6,084,683 A | 7/2000 | Bruno et al. | |
| 6,580,506 B2 | 6/2003 | Inman, Jr. | |
| 6,661,512 B2 | 12/2003 | Fernando et al. | |
| 7,414,116 B2 | 8/2008 | Milton et al. | |
| 7,817,277 B2 | 10/2010 | Crist et al. | |
| 8,906,320 B1 | 12/2014 | Eltoukhy et al. | |
| 9,012,022 B2 | 4/2015 | George et al. | |
| 9,453,258 B2 | 9/2016 | Kain et al. | |
| 9,512,422 B2 | 12/2016 | Barnard et al. | |
| 10,254,225 B2 | 4/2019 | Zhong et al. | |
| 11,143,638 B2 | 10/2021 | Khurana et al. | |
| 11,402,358 B2 | 8/2022 | Khurana et al. | |
| 2003/0086823 A1 | 5/2003 | Fernando et al. | |
| 2003/0197125 A1 | 10/2003 | De Saro et al. | |
| 2007/0039866 A1* | 2/2007 | Schroeder | C12Q 1/6869 |
| | | | 210/265 |
| 2010/0157291 A1* | 6/2010 | Kiesel | G01N 15/1429 |
| | | | 356/244 |
| 2011/0318820 A1* | 12/2011 | Hinz | G01N 27/4145 |
| | | | 435/287.2 |
| 2015/0261664 A1 | 9/2015 | Goldman et al. | |
| 2016/0011098 A1* | 1/2016 | Graham | G01N 15/1434 |
| | | | 156/196 |
| 2016/0273032 A1 | 9/2016 | Esfandyarpour et al. | |
| 2016/0289669 A1 | 10/2016 | Fan et al. | |
| 2017/0144155 A1 | 5/2017 | Bohm et al. | |
| 2017/0145497 A1 | 5/2017 | Rothberg et al. | |
| 2017/0189904 A1 | 7/2017 | Aravanis et al. | |
| 2018/0033510 A1* | 2/2018 | Archibald | C07B 59/00 |
| 2018/0117587 A1 | 5/2018 | Lemoine et al. | |
| 2018/0187252 A1 | 7/2018 | Hunter et al. | |
| 2018/0250672 A1 | 9/2018 | Jamshidi et al. | |
| 2022/0317100 A1 | 10/2022 | Khurana et al. | |

FOREIGN PATENT DOCUMENTS

| | | |
|---|---|---|
| WO | WO 2010/008480 A2 | 1/2010 |
| WO | WO 2014/151961 A1 | 9/2014 |
| WO | WO 2015/031849 A1 | 3/2015 |
| WO | WO 2015/040930 A1 | 3/2015 |
| WO | WO 2017/030999 A1 | 2/2017 |
| WO | WO 2018/128777 A1 | 7/2018 |
| WO | WO 2018/136509 A1 | 7/2018 |

OTHER PUBLICATIONS

International Search Report and Written Opinion dated Aug. 25, 2020, for International Application No. PCT/US2020/034518, 8 pages.

* cited by examiner

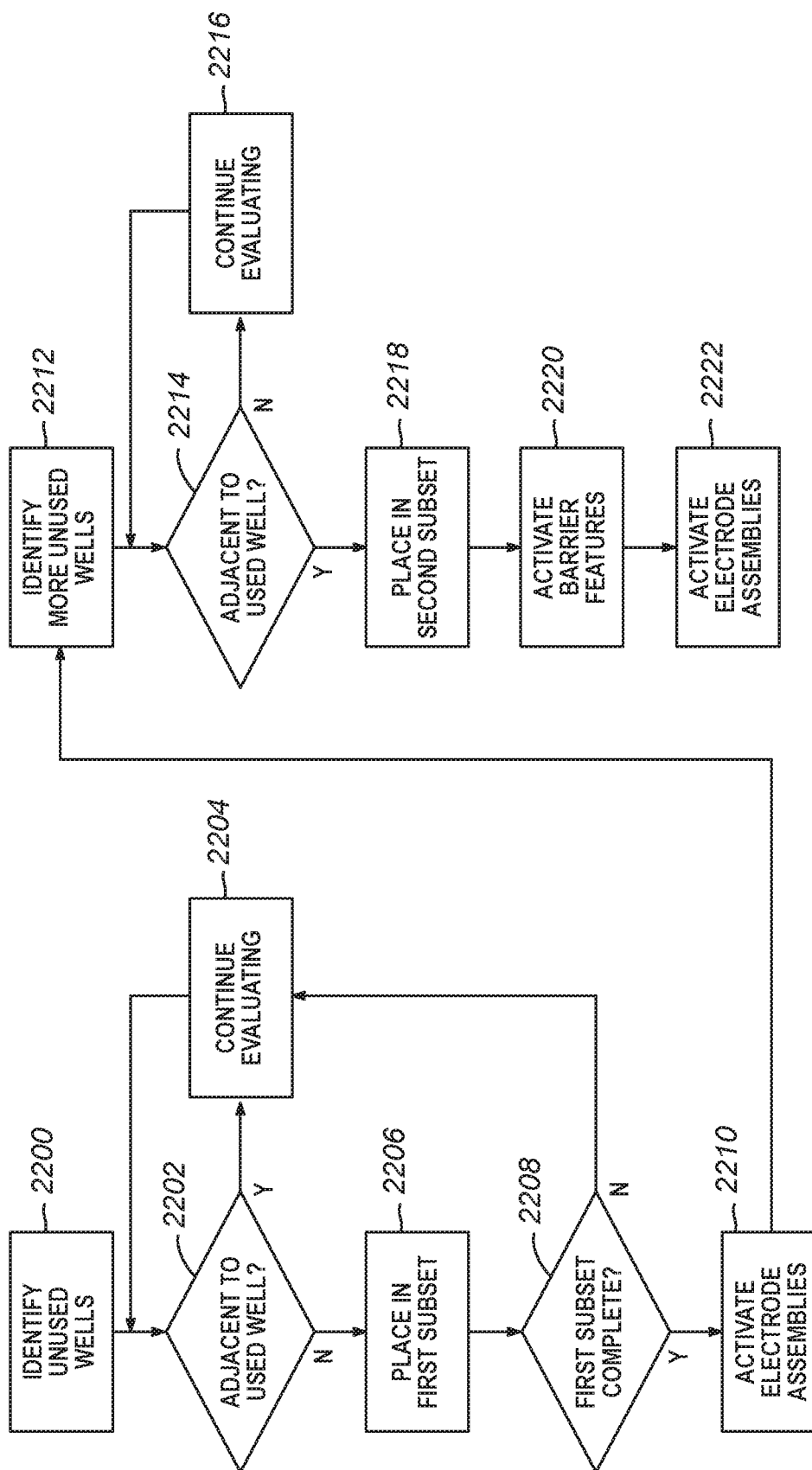

FLOW CELL WITH ONE OR MORE BARRIER FEATURES

RELATED APPLICATIONS

This application is a continuation of U.S. patent application Ser. No. 17/846,538, entitled "Flow Cell with One or More Barrier Features," filed on Jun. 22, 2022, which is a continuation of U.S. patent application Ser. No. 17/479,342, entitled "Flow Cell with One or More Barrier Features," filed on Sep. 20, 2021, issued as U.S. Pat. No. 11,402,358, which is a continuation of U.S. patent application Ser. No. 17/254,466, entitled "Flow Cell with One or More Barrier Features," filed on Dec. 21, 2021, issued as U.S. Pat. No. 11,143,638 on Oct. 12, 2021, which is a national stage entry of International Patent Application No. PCT/US2020/034518, entitled "Flow Cell with One or More Barrier Features," filed on May 26, 2020, which claims priority to U.S. Provisional Patent App. No. 62/855,654, entitled "Flow Cell with One or More Barrier Features In or Between Wells," filed on May 31, 2019, which is incorporated by reference herein in its entirety. International Patent Application No. PCT/US2020/034518 also claims priority to U.S. Provisional Patent App. No. 62/855,662, entitled "Flow Cell with Barrier Features to Prevent Optical Cross-Talk Between Wells," filed on May 31, 2019, which is incorporated by reference herein in its entirety.

BACKGROUND

Computer systems have used various different mechanisms to store data, including magnetic storage, optical storage, and solid-state storage. Such forms of data storage may present drawbacks in the form of read-write speed, duration of data retention, power usage, or data density.

Just as naturally occurring DNA may be read, machine-written DNA may also be read. Pre-existing DNA reading techniques may include an array-based, cyclic sequencing assay (e.g., sequencing-by-synthesis (SBS)), where a dense array of DNA features (e.g., template nucleic acids) are sequenced through iterative cycles of enzymatic manipulation. After each cycle, an image may be captured and subsequently analyzed with other images to determine a sequence of the machine-written DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

SUMMARY

Described herein are devices, systems, and methods for containing reactions within wells of a DNA storage device and to prevent or otherwise reduce diffusion between wells of the DNA storage device.

An implementation relates to an apparatus comprising a flow cell body. In some such implementations, the flow call body may define one or more flow channels and a plurality of wells, each channel of the one or more flow channels to receive a fluid. In some such implementations, each well of the plurality of wells may be fluidically coupled with the corresponding flow channel of the one or more flow channels, and each well of the plurality of wells may define a corresponding depth. In some such implementations, the apparatus may also comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may also comprise an imaging assembly to capture images indicative of one or more nucleotides in a polynucleotide. In some such implementations, the apparatus may comprise one or more barrier features positioned in or between the plurality of wells, the barrier features to contain reactions in each well of the plurality of wells or reduce diffusion between the plurality of wells.

Variations on any one or more of the above implementations exist, wherein each electrode of the plurality of electrodes may define an aperture.

Variations on any one or more of the above implementations exist, wherein the imaging assembly may include at least one image sensor to receive light through the aperture of each electrode of the plurality of electrodes.

Variations on any one or more of the above implementations exist, wherein each electrode of the plurality of electrodes may be annularly shaped.

Variations on any one or more of the above implementations exist, wherein each electrode of the plurality of electrodes may comprise a plurality of electrode segments arranged in quadrants, the aperture being defined at a central region of the arrangement of quadrants.

Variations on any one or more of the above implementations exist, wherein the apparatus may further comprise an integrated circuit positioned under the flow cell body, the integrated circuit to drive the electrodes to thereby effect writing of polynucleotides in the corresponding wells of the plurality of wells.

Variations on any one or more of the above implementations exist, wherein the integrated circuit may be further in communication with the imaging assembly.

Variations on any one or more of the above implementations exist, wherein the integrated circuit may comprise a complementary metal-oxide-semiconductor (CMOS) chip.

Variations on any one or more of the above implementations exist, wherein the plurality of wells may be formed as a plurality of discrete recesses arranged in a pattern along a base surface of the corresponding flow channel of the one or more flow channels.

Variations on any one or more of the above implementations exist, wherein each well of the plurality of wells may be defined by at least one sidewall and a floor.

Variations on any one or more of the above implementations exist, wherein each electrode of the plurality of electrodes may be positioned on the floor of the corresponding well of the plurality of wells.

Variations on any one or more of the above implementations exist, wherein each electrode of the plurality of electrodes may be positioned on a sidewall of the at least one sidewall of the corresponding well of the plurality of wells.

Variations on any one or more of the above implementations exist, wherein the floor of each well of the plurality of wells may further define an opening, the opening to provide a path for fluid communication between the corresponding well of the plurality of wells and a fluid source.

Variations on any one or more of the above implementations exist, wherein the barrier features may comprise a plurality of valves, each valve of the plurality of valves being positioned in the opening of each corresponding well of the plurality of wells.

Variations on any one or more of the above implementations exist, wherein each valve of the plurality of valves may comprise a hydrogel material.

Variations on any one or more of the above implementations exist, wherein the hydrogel material to transition between an expanded state and a contracted state, the hydrogel material to effectively close the aperture of the well of the plurality of wells in the expanded state, the hydrogel material to effectively open the aperture of the well of the plurality wells in the contracted state.

Variations on any one or more of the above implementations exist, wherein each valve of the plurality of valves may comprise a hydrogel ring defining an opening aligned with the aperture of the corresponding well of the plurality of wells.

Variations on any one or more of the above implementations exist, wherein each valve of the plurality of valves may comprise an electroactive polymer material.

Variations on any one or more of the above implementations exist, wherein each valve of the plurality of valves to transition between an open state and a closed state in response to changes in pH. In some such implementations, the apparatus may further comprise a pH driving feature to thereby selectively transition the valve of the plurality of valves between the open state and the closed state.

Variations on any one or more of the above implementations exist, wherein each valve of the plurality of valves to transition between an open state and a closed state in response to changes in temperature. In some such implementations, the apparatus may further comprise a temperature driving feature to selectively vary a temperature value associated with each valve of the plurality of valves to thereby selectively transition the valve of the plurality of valves between the open state and the closed state.

Variations on any one or more of the above implementations exist, wherein each valve of the plurality of valves may comprise a heat swellable polymer.

Variations on any one or more of the above implementations exist, wherein each valve of the plurality of valves being biased toward a closed state, each valve of the plurality of valves to open in response to fluid pressure against the valve of the plurality of valves exceeding a threshold.

Variations on any one or more of the above implementations exist, wherein the apparatus may further comprise a control module to control opening and closing of each valve of the plurality of valves.

Variations on any one or more of the above implementations exist, wherein the control module to selectively activate the plurality of valves to allow deblocking agent to pass through the apertures of the plurality of wells.

Variations on any one or more of the above implementations exist, wherein the one or more barrier features may include a flow gradient generator, the flow gradient generator to provide a fluid flow profile that varies across the depth of each well of the plurality of wells.

Variations on any one or more of the above implementations exist, wherein the flow gradient generator to provide a reduced flow of fluid or fluid pressure at a bottom region of each well of the plurality of wells, with an increased flow of fluid or fluid pressure at a top region of each well of the plurality of wells.

Variations on any one or more of the above implementations exist, wherein the flow gradient generator may comprise a pump.

Variations on any one or more of the above implementations exist, wherein the flow gradient generator may comprise a bubble generator.

Variations on any one or more of the above implementations exist, wherein the one or more barrier features may include a temperature gradient generator, the temperature gradient generator to provide a temperature profile that varies across the depth of each well of the plurality of wells.

Variations on any one or more of the above implementations exist, wherein the temperature gradient generator to provide a relatively higher temperature in a bottom region of each well of the plurality of wells and a relatively lower temperature in a top region of each well of the plurality of wells.

Variations on any one or more of the above implementations exist, wherein the one or more barrier features may include a temperature gradient generator, the temperature gradient generator to provide a temperature profile that varies between the plurality of wells.

Variations on any one or more of the above implementations exist, wherein the temperature gradient generator to provide a relatively higher temperature within each well of the plurality of wells and a relatively lower temperature in spaces between the plurality of wells.

Variations on any one or more of the above implementations exist, wherein the one or more barrier features may comprise a plurality of hydrophobic partitions positioned along a base surface of the flow cell body between adjacent wells of the plurality of wells.

Variations on any one or more of the above implementations exist, wherein the plurality of hydrophobic partitions may extend from the base surface of the flow cell body toward an upper surface of the flow cell body.

Variations on any one or more of the above implementations exist, wherein the plurality of hydrophobic partitions to transition from positions along the base surface of the flow cell body between adjacent wells of the plurality of wells to positions over each corresponding well of the plurality of wells, such that the plurality of hydrophobic partitions are to transition from being barriers between the plurality of wells to being caps over the plurality of wells.

Variations on any one or more of the above implementations exist, wherein the plurality of hydrophobic partitions to move in response to an applied voltage.

Variations on any one or more of the above implementations exist, wherein each hydrophobic partition of the plurality of hydrophobic partitions to cover a two more wells of the plurality of wells simultaneously.

Variations on any one or more of the above implementations exist, wherein each hydrophobic partition of the plurality of hydrophobic partitions to cover only a single well of the plurality of wells, such that each of the plurality of wells has a respective hydrophobic partition of the plurality of hydrophobic partitions.

Variations on any one or more of the above implementations exist, wherein each hydrophobic partition of the plurality of hydrophobic partitions may comprise a volume of a fluid.

Variations on any one or more of the above implementations exist, wherein each hydrophobic partition of the plurality of hydrophobic partitions may comprise a volume of an oil.

Variations on any one or more of the above implementations exist, wherein the one or more barrier features may comprise a pH driving feature to selectively adjust pH values associated with each well of the plurality of wells to thereby provide variation in pH values among adjacent wells of the plurality of wells.

Variations on any one or more of the above implementations exist, wherein pH driving feature may comprise a bubble generator.

Variations on any one or more of the above implementations exist, wherein the pH driving feature may comprise electrodes.

Variations on any one or more of the above implementations exist, wherein the plurality of electrodes to effect writing of polynucleotides in the form of DNA strands in the corresponding wells of the plurality of wells.

Variations on any one or more of the above implementations exist, wherein the plurality of electrodes may include electrodes positioned in a bottom region of each well of the plurality of wells, the electrodes positioned in the bottom region of each well of the plurality of wells to drive a redox reaction within the corresponding well of the plurality of wells.

Variations on any one or more of the above implementations exist, wherein each electrode of the electrodes positioned in the bottom region of each well of the plurality of wells may comprise a copper element.

Variations on any one or more of the above implementations exist, wherein the plurality of electrodes may further include electrodes positioned on surfaces of interstitial spaces between wells of the plurality of wells, the electrodes on surfaces of interstitial spaces between wells of the plurality of wells providing the one or more barrier features.

Variations on any one or more of the above implementations exist, wherein the electrodes positioned on surfaces of interstitial spaces between wells of the plurality of wells to provide a reverse current that sharpens boundaries defined by the electrodes positioned in the bottom region of each well of the plurality of wells.

Another implementation relates to an apparatus comprising a body defining an upper flow channel a plurality of wells, the upper flow channel to receive a flow of fluid containing nucleotides. In some such implementations, each well of the plurality of wells may be fluidically coupled with the corresponding flow channel, and each well of the plurality of wells may have a floor with an aperture. In some such implementations, the apparatus may comprise a lower channel positioned under the floor of each well of the plurality of wells, the lower channel to receive fluid containing a deblocking agent. In some such implementations, the apparatus may comprise a plurality of valves. In some such implementations, each valve of the plurality of valves to transition between an open and closed state, each valve of the plurality of valves to permit fluid communication between the lower channel and the corresponding well of the plurality of wells in the open state, each valve of the plurality of valves to reduce fluid communication between the lower channel and the corresponding well of the plurality of wells in the closed state. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells.

Variations on any one or more of the above implementations exist, wherein the apparatus may further comprise an imaging assembly to capture images indicative of one or more nucleotides in a polynucleotide.

Variations on any one or more of the above implementations exist, wherein each valve of the plurality of valves may comprise a hydrogel material.

Variations on any one or more of the above implementations exist, wherein each valve of the plurality of valves may comprise an electroactive polymer.

Variations on any one or more of the above implementations exist, wherein each valve of the plurality of valves may comprise a heat swellable polymer.

Variations on any one or more of the above implementations exist, wherein each valve of the plurality of valves may be biased toward a closed state, each valve of the plurality of valves to open in response to fluid pressure against the valve exceeding a threshold.

Yet another implementation relates to an apparatus comprising a flow cell body. In some such implementations, the flow cell body may define one or more flow channels and a plurality of wells, each flow channel of the one or more flow channels to receive a flow of fluid. In some such implementations, each well of the plurality of wells may be fluidically coupled with the corresponding flow channel of the one or more flow channels, and each well of the plurality of wells may define a corresponding depth. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise a flow gradient generator, the flow gradient generator to provide a fluid flow profile that varies across the depth of each well of the plurality of wells.

Variations on any one or more of the above implementations exist, wherein the apparatus may further comprise an imaging assembly to capture images indicative of one or more nucleotides in a polynucleotide.

Variations on any one or more of the above implementations exist, wherein the flow gradient generator to provide a reduced flow of fluid or fluid pressure at a bottom region of each well of the plurality of wells, with an increased flow of fluid or fluid pressure at a top region of each well of the plurality of wells.

Yet another implementation relates to an apparatus comprising a flow cell body. In some such implementations, the flow cell body may define one or more flow channels and a plurality of wells, each flow channel of the one or more flow channels to receive a flow of fluid. In some such implementations, each well of the plurality of wells may be fluidically coupled with the corresponding flow channel of the one or more flow channels, and each well of the corresponding wells defining a corresponding depth. In some such implementations, the apparatus may comprise a plurality of electrodes. In some such implementations, each electrode from the plurality of electrodes may be positioned in a corresponding well of the plurality of wells, the plurality of electrodes to effect writing of polynucleotides in the corresponding wells of the plurality of wells. In some such implementations, the apparatus may comprise a temperature gradient generator, the temperature gradient generator to provide a temperature profile that varies across the depth of each well of the plurality of wells.

Variations on any one or more of the above implementations exist, wherein the apparatus may further comprise an imaging assembly to capture images indicative of one or more nucleotides in a polynucleotide.

Variations on any one or more of the above implementations exist, wherein the temperature gradient generator to provide a relatively higher temperature in a bottom region of each well of the plurality of wells and a relatively lower temperature in a top region of each well of the plurality of wells.

Yet another implementation relates to an apparatus comprising a flow cell body defining one or more channels and a plurality of wells, each flow channel of the one or more flow channels to receive a flow of fluid. In some such implementations, each well of the plurality of wells may be fluidically coupled with the corresponding flow channel of the one or more flow channels, each well of the plurality of wells defining a corresponding depth. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise a temperature gradient generator, the temperature gradient generator to provide a temperature profile that varies between the plurality of wells.

Variations on any one or more of the above implementations exist, wherein the apparatus may further comprise an imaging assembly to capture images indicative of one or more nucleotides in a polynucleotide.

Variations on any one or more of the above implementations exist, wherein the temperature gradient generator to provide a relatively higher temperature within each well of the plurality of wells, and a relatively lower temperature in spaces between the plurality of wells.

Yet another implementation relates to an apparatus comprising a flow cell body defining one or more flow channels, an upper surface, a base surface, and a plurality of wells formed in the base surface, each flow channel of the one or more flow channels to receive a flow of fluid, each well of the plurality of wells being fluidically coupled with the corresponding flow channel of the one or more flow channels. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise a plurality of hydrophobic partitions positioned along the base surface of the flow cell body between adjacent wells of the plurality of wells. In some such implementations, the plurality of hydrophobic partitions may extend from the base surface of the flow cell body toward an upper surface of the flow cell body.

Variations on any one or more of the above implementations exist, wherein the apparatus may further comprise an imaging assembly to capture images indicative of one or more nucleotides in a polynucleotide.

Variations on any one or more of the above implementations exist, wherein the plurality of hydrophobic partitions to move from positions along the floor of the flow cell body between adjacent wells of the plurality of wells to positions over each corresponding well of the plurality of wells, such that the plurality of hydrophobic partitions are to transition from being barriers between the plurality of wells to being caps over the plurality of wells.

Variations on any one or more of the above implementations exist, wherein the plurality of hydrophobic partitions to move in response to an applied voltage.

Variations on any one or more of the above implementations exist, wherein each hydrophobic partition of the plurality of hydrophobic partitions may comprise a volume of fluid.

Yet another implementation relates to an apparatus comprising a flow cell body defining one or more channels, an upper surface, a base surface, and a plurality of wells formed in the base surface, each flow channel of the one or more flow channels to receive a flow of fluid. In some such implementations, each well of the plurality of wells may be fluidically coupled with the one or more flow channels. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise a pH driving feature to selectively adjust pH values associated with each well of the plurality of wells to thereby provide variation in pH values among adjacent wells of the plurality of wells.

Variations on any one or more of the above implementations exist, wherein the apparatus may further comprise an imaging assembly to capture images of polynucleotides written in the wells of the plurality of wells.

Variations on any one or more of the above implementations exist, wherein the pH driving feature may comprise a device selected from the group consisting of a bubble generator and a set of electrodes.

An implementation relates to an apparatus comprising a flow cell body defining one or more flow channels, each flow channel of the one or more flow channels to receive a flow of fluid. In such implementations, at least one of the one or more flow channels may have a floor and a plurality of wells defined as recesses in the floor, each well of the plurality of wells being fluidically coupled with the corresponding flow channel, the flow cell body further defining interstitial spaces between adjacent wells of the plurality of wells. In some such implementations, the apparatus may comprise a plurality of electrode assemblies. In some such implementations, each electrode assembly of the plurality of electrode assemblies may be positioned in a corresponding well of the plurality of wells, the plurality of electrode assemblies to generate machine-written polynucleotides in the corresponding wells of the plurality of wells. In some such implementations, the apparatus may comprise one or more barrier features positioned above the plurality of wells or in the plurality of wells, the one or more barrier features to reduce optical cross-talk between the plurality of wells.

Variations on any one or more of the above implementations exist, wherein the apparatus may further comprise an imaging assembly to capture images indicative of one or more nucleotides in machine-written polynucleotides written in the wells of the plurality of wells.

Variations on any one or more of the above implementations exist, wherein the one or more barrier features may comprise an electrically activated polarizer.

Variations on any one or more of the above implementations exist, wherein each of the polarizers may be positioned in an upper region of a corresponding well of the plurality of wells.

Variations on any one or more of the above implementations exist, wherein each of the polarizers may define an opening to permit fluid to flow from the at least one of the one or more flow channels into the corresponding well of the plurality of wells.

Variations on any one or more of the above implementations exist, wherein the apparatus may further comprise a light source, the light source to project light to two or more wells of the plurality of wells that are positioned to simultaneously receive the light projected from the light source.

Variations on any one or more of the above implementations exist, wherein the polarizers to selectively permit or restrict passage of light from the light source to the two or more wells that are positioned to simultaneously receive the light projected from the light source.

Variations on any one or more of the above implementations exist, wherein the one or more barrier features may comprise photoguides.

Variations on any one or more of the above implementations exist, wherein the plurality of electrode assemblies to generate machine-written polynucleotides in the form of DNA strands.

Another implementation relates to a method comprising flowing fluid through a flow cell. In some such implementations, the flow may contain nucleotides, and the flow cell may comprise a flow cell body defining one or more flow channels, each flow channel of the one or more flow channels to receive a flow of fluid. In some such implementations, at least one of the one or more flow channels may have a floor, a plurality of wells defined as recesses in the floor, and a plurality of barriers above the wells of the plurality of wells or in the wells of the plurality of wells. In some such implementations, each well of the plurality of wells may be fluidically coupled with the corresponding flow channel of the one or more flow channels, and the floor of the flow channel of the one or more flow channels may interstitial spaces between adjacent wells of the plurality of wells. In some such implementations, the method may comprise activating electrode assemblies at bottom regions of each well of the plurality of wells to generate machine-written polynucleotides within each well of the plurality of wells, the machine-written polynucleotides representing stored data. In some such implementations, the method may comprise activating the plurality of barrier features to reduce optical cross-talk between adjacent wells of the plurality of wells.

Variations on any one or more of the above implementations exist, wherein activating the electrode assemblies at the bottom region of each well of the plurality of wells may comprise generating a positive current and activating the plurality of barrier features may comprise generating a negative current.

Variations on any one or more of the above implementations exist, wherein activating the plurality of barrier features may comprise adding a charge tag to at least some of the nucleotides.

Variations on any one or more of the above implementations exist, wherein each charge tag may be positively charged.

Variations on any one or more of the above implementations exist, wherein each charge tag may impart a net positive charge to the corresponding nucleotide of the nucleotides.

Variations on any one or more of the above implementations exist, wherein each charge tag may be negatively charged.

Variations on any one or more of the above implementations exist, wherein each charge tag may be attached to one or more regions of the corresponding nucleotide of the nucleotides selected from a ribose, a phosphate group, or a base.

Variations on any one or more of the above implementations exist, wherein each charge tag may be cleaved before a ligation event.

Variations on any one or more of the above implementations exist, wherein each charge tag may be cleaved after a ligation event.

Yet another implementation relates to a method comprising flowing a fluid through a flow cell, the fluid containing nucleotides. In some such implementations, the flow cell may comprise a flow cell body defining one or more flow channels, each flow channel of the one or more flow channels to receive a flow of fluid. In some such implementations, each flow channel of the one or more flow channels may have a floor, and a plurality of wells defined as recesses in the floor. In some such implementations, each well of the plurality of wells may be fluidically coupled with the corresponding flow channel of the one or more flow channels, the floor of the flow channel of the one or more flow channels defining interstitial surfaces between adjacent wells of the plurality of wells. In some such implementations, each flow channel of the one or more flow channels may have a plurality of barrier features positioned above the plurality of wells or in the plurality of wells, the plurality of barrier features to reduce optical cross-talk between the plurality of wells. In some such implementations, the method may comprise determining a first subset of the plurality of wells that are unused, and that are not adjacent to a used well of the plurality of wells. In some such implementations, the method may comprise activating electrode assemblies at bottom regions of each well of the first subset to generate machine-written polynucleotides within each well of the first subset, the machine-written polynucleotides within each well of the first subset representing stored data, while leaving the plurality of barrier features deactivated. In some such implementations, the method may comprise determining a second subset of the plurality of wells that are unused, but that are adjacent to a used well of the plurality of wells. In some such implementations, the method may comprise activating electrode assemblies at bottom regions of each well of the second subset to generate machine-written polynucleotides within each well of the second subset, the machine-written polynucleotides the machine-written polynucleotides within each well of the second subset representing stored data, after activating the barrier features to reduce optical cross-talk between adjacent wells of the plurality of wells.

Variations on any one or more of the above implementations exist, wherein the method may comprise receiving a request for stored data. In some such implementations, the method may comprise determining a set of target wells from the plurality of wells in which the stored data is represented by machine-written polynucleotides. In some such implementations, the method may comprise determining whether each well of the set of target wells is adjacent to any used wells of the plurality of wells. In some such implementations, the method may comprise, where a target well of the set of target wells is adjacent to any used well, activating an integrated circuit to detect fluorescence emitted from a fluorophore of a machine-written polynucleotide and read the stored data from the target well of the set of target wells that is adjacent to a used well, after activating the barrier features to reduce optical cross-talk with the adjacent wells of the plurality of wells.

Variations on any one or more of the above implementations exist, wherein the method may comprise, where the target well is adjacent to any used well, performing a cross-talk quality control check on the read stored data. In some such implementations, the method may comprise, where the cross-talk quality control check verifies that that read stored data is not corrupted, providing the read stored data to a requesting device.

Variations on any one or more of the above implementations exist, wherein the method may comprise receiving a request for stored data. In some such implementations, the method may comprise determining a set of target wells from the plurality of wells in which the stored data is represented by machine-written polynucleotides. In some such implementations, the method may comprise determining whether each well of the set of target wells is adjacent to any used wells of the plurality of wells. In some such implementations, the method may comprise, where a target well of the set of target wells is not adjacent to any used well, activating an integrated circuit to detect fluorescence of emitted from a fluorophore of a machine-written polynucleotide and read the stored data from the target well of the set of target wells that is adjacent to a used well, while leaving the barrier features deactivated.

Variations on any one or more of the above implementations exist, wherein the method may further comprise, where the target well is not adjacent to any used well of the plurality of wells, providing the read stored data to a requesting device without performing a cross talk quality control check on the read stored data.

It should be appreciated that all combinations of the foregoing concepts and additional concepts discussed in greater detail below (provided such concepts are not mutually inconsistent) are contemplated as being part of the inventive subject matter disclosed herein and to achieve the benefits/advantages as described herein. In particular, all combinations of claimed subject matter appearing at the end of this disclosure are contemplated as being part of the inventive subject matter disclosed herein.

BRIEF DESCRIPTION OF THE DRAWINGS

The details of one or more implementations are set forth in the accompanying drawings and the description below. Other features, aspects, and advantages will become apparent from the description, the drawings, and the claims, in which:

FIG. 21 depicts a flow chart showing an example of a method that may be performed while machine-writing DNA.

Figure 1:
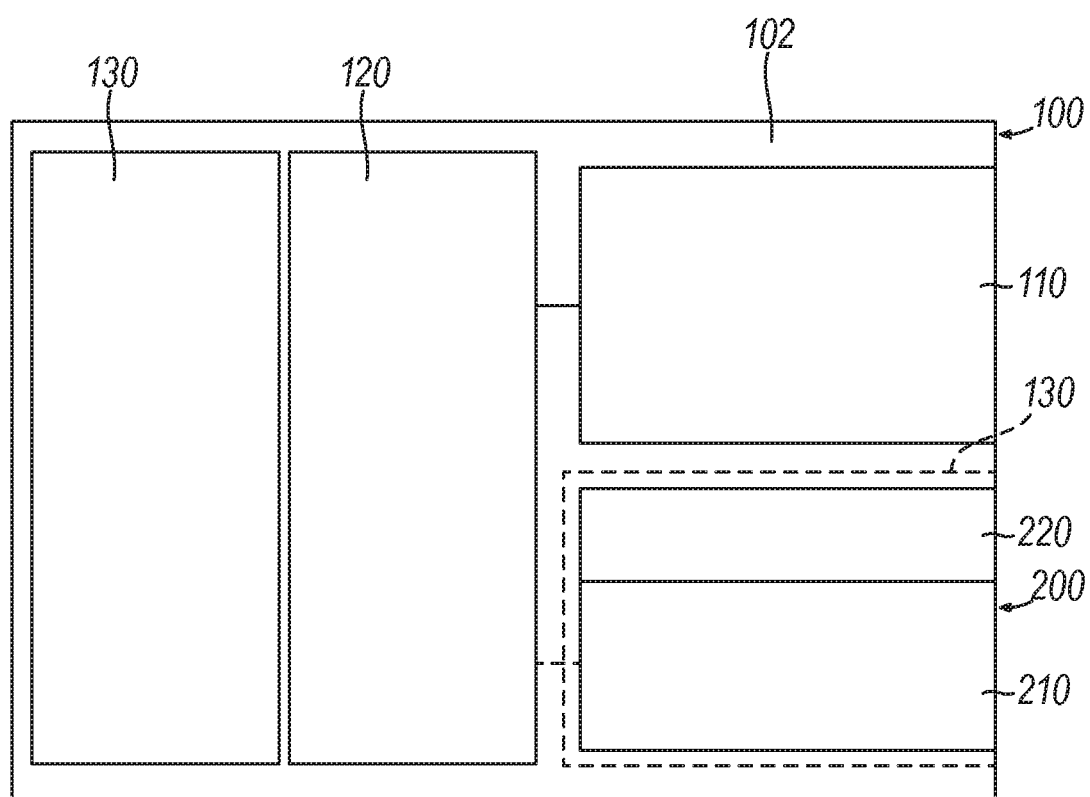
FIG. 1 depicts a block schematic view of an example of a system that may be used to conduct biochemical processes.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

In some aspects, methods and systems are disclosed herein for synthesizing DNA (or other biological material) to store data or other information; and/or reading machine-written DNA (or other biological material) to retrieve the machine-written data or other information. Machine-written DNA may provide an alternative to traditional forms of data storage (e.g., magnetic storage, optical storage, and solid-state storage). In some aspects, methods and systems are disclosed herein for preventing optical cross-talk between adjacent wells of a flow cell while synthesizing DNA (or other biological material) to store data or other information; and/or reading machine-written DNA (or other biological material) to retrieve the machine-written data or other information. Machine-written DNA may provide faster read-write speeds, longer data retention, reduced power usage, and higher data density. Examples of how digital information may be stored in DNA are disclosed in U.S. Pub. No. 2015/0261664, entitled "High-Capacity of Storage of Digital Information in DNA," published Sep. 17, 2015, which is incorporated by reference herein in its entirety. For example, methods from code theory to enhance the recoverability of the encoded messages from the DNA segment, including forbidding DNA homopolymers (i.e. runs of more than one identical base) that are known to be associated with higher error rates in existing high throughput technologies may be used. Further, an error-detecting component, analogous to a parity-check bit, may be integrated into the indexing information in the code. More complex schemes, including but not limited to error-correcting codes and, indeed, substantially any form of digital data security (e.g., RAID-based schemes) currently employed in informatics, may be implemented in future developments of the DNA storage scheme. The DNA encoding of information may be computed using software. The bytes comprising each computer file may be represented by a DNA sequence with no homopolymers by an encoding scheme to produce an encoded file that replaces each byte by five or six bases forming the DNA sequence.

The code used in the encoding scheme may be constructed to permit a straightforward encoding that is close to the optimum information capacity for a run length-limited channel (e.g., no repeated nucleotides), though other encoding schemes may be used. The resulting in silico DNA sequences may be too long to be readily produced by standard oligonucleotide synthesis and may be split into overlapping segments of a length of 100 bases with an overlap of 75 bases. To reduce the risk of systematic synthesis errors introduced to any particular run of bases, alternate ones of the segments may be converted to their reverse complement, meaning that each base may be "written" four times, twice in each direction. Each segment may then be augmented with an indexing information that permits determination of the computer file from which the segment originated and its location within that computer file, plus simple error-detection information. This indexing information may also be encoded in as non-repeating DNA nucleotides and appended to the information storage bases of the DNA segments. The division of the DNA segments into lengths of 100 bases with an overlap of 75 bases is purely arbitrary and illustrative, and it is understood that other lengths and overlaps may be used and is not limiting.

Other encoding schemes for the DNA segments may be used, for example to provide enhanced error-correcting properties. The amount of indexing information may be increased in order to allow more or larger files to be encoded. One extension to the coding scheme in order to avoid systematic patterns in the DNA segments may be to add change the information. One way may use the "shuffling" of information in the DNA segments, where the information may be retrieved if one knows the pattern of shuffling. Different patterns of shuffles may be used for different ones of the DNA segments. A further way is to add a degree of randomness into the information in each one of the DNA segments. A series of random digits may be used for this, using modular addition of the series of random digits and the digits comprising the information encoded in the DNA segments. The information may be retrieved by modular subtraction during decoding if one knows the series of random digits used. Different series of random digits may be used for different ones of the DNA segments The data-encoding component of each string may contain Shannon information at 5.07 bits per DNA base, which is close to the theoretical optimum of 5.05 bits per DNA base for base-4 channels with run length limited to one. The indexing implementation may permit $3^{14}=4782969$ unique data locations. Increasing the number of indexing trits (and therefore bases) used to specify file and intra-file location by just two, to 16, gives $3^{16}=43046721$ unique locations, in excess of the 16.8M that is the practical maximum for the Nested Primer Molecular Memory (NPMM) scheme.

The DNA segment designs may be synthesized in three distinct runs (with the DNA segments randomly assigned to runs) to create approx. $1.2 \times 10^7$ copies of each DNA segment design. Phosphoramidite chemistry may be used, and inkjet printing and flow cell reactor technologies in an in-situ microarray synthesis platform may be employed. The inkjet printing within an anhydrous chamber may allow the delivery of very small volumes of phosphoramidites to a confined coupling area on a 2D planar surface, resulting in the addition of hundreds of thousands of bases in parallel. Subsequent oxidation and detritylation may be carried out in a flow cell reactor. Once DNA synthesis is completed, the oligonucleotides may then be cleaved from the surface and deprotected.

Adapters may then be added to the DNA segments to enable a plurality of copies of the DNA segments to be made. A DNA segment with no adapter may require additional chemical processes to "kick start" the chemistry for the synthesis of the multiple copies by adding additional groups onto the ends of the DNA segments. Oligonucleotides may be amplified using polymerase chain reaction (PCR) methods and paired-end PCR primers, followed by bead purification and quantification. Oligonucleotides may then be sequenced to produce reads of 104 bases. The digital information decoding may then be carried out via sequencing of the central bases of each oligo from both ends and rapid computation of full-length oligos and removal of sequence reads inconsistent with the designs. Sequence reads may be decoded using computer software that exactly reverses the encoding process. Sequence reads for which the parity-check trit indicates an error or that may be unambiguously decoded or assigned to a reconstructed computer file may be discarded. Locations within every decoded file may be detected in multiple different sequenced DNA oligos, and simple majority voting may be used to resolve any discrepancies caused by the DNA synthesis or the sequencing errors.

While several examples herein are provided in the context of machine-written DNA, it is contemplated that the principles described herein may be applied to other kinds of machine-written biological material.

As used herein, the term "machine-written DNA" shall be read to include one or more strands of polynucleotides that are generated by a machine, or otherwise modified by a machine, to store data or other information. One example of the polynucleotide herein is a DNA. It is noted that while the term "DNA" in the context of DNA being read or written is used throughout this disclosure, the term is used only as a representative example of a polynucleotide and may encompass the concept of a polynucleotide. "Machine," as used herein in reference to "machine-written," may include an instrument or system specially designed for writing DNA as described in greater detail herein. The system may be non-biological or biological. In one example, the biological system may comprise, or is, a polymerase. For example, the polymerase may be terminal deoxynucleotidyl transferase (TdT). In a biological system, the process may be additionally controlled by a machine hardware (e.g., processor) or an algorithm. "Machine-written DNA" may include any polynucleotide having one or more base sequences written by a machine. While machine-written DNA is used herein as an example, other polynucleotide strands may be substituted for machine-written DNA described herein. "Machine-written DNA" may include natural bases and modifications of natural bases, including but not limited to bases modified with methylation or other chemical tags; an artificially synthesized polymer that is similar to DNA, such as peptide nucleic acid (PNA); or Morpholino DNA. "Machine-written DNA" may also include DNA strands or other polynucleotides that are formed by at least one strand of bases originating from nature (e.g., extracted from a naturally occurring organism), with a machine-written strand of bases secured thereto either in a parallel fashion or in an end-to-end fashion. In other implementations, "machine-written DNA" may be written by a biological system (e.g., enzyme) in lieu of, or in addition to, a non-biological system (e.g., the electrode machine) writing of DNA described herein. In other words, "machine-written DNA" may be written directly by a machine; or by an enzyme (e.g., polymerase) that is controlled by an algorithm and/or machine.

"Machine-written DNA" may include data that have been converted from a raw form (e.g., a photograph, a text document, etc.) into a binary code sequence using known techniques, with that binary code sequence then being converted to a DNA base sequence using known techniques, and with that DNA base sequence then being generated by a machine in the form of one or more DNA strands or other polynucleotides. Alternatively, "machine-written DNA" may be generated to index or otherwise track pre-existing DNA, to store data or information from any other source and for any suitable purpose, without necessarily requiring an intermediate step of converting raw data to a binary code.

As described in greater detail below, machine-written DNA may be written to and/or read from a reaction site. As used herein, the term "reaction site" is a localized region where at least one designated reaction may occur. A reaction site may include support surfaces of a reaction structure or substrate where a substance may be immobilized thereon. For instance, the reaction site may be a discrete region of space where a discrete group of DNA strands or other polynucleotides are written. The reaction site may permit chemical reactions that are isolated from reactions that are in adjacent reaction sites. Devices that provide machine-writing of DNA may include flow cells with wells having writing features (e.g., electrodes) and/or reading features. In some instances, the reaction site may include a surface of a reaction structure (which may be positioned in a channel of a flow cell) that already has a reaction component thereon, such as a colony of polynucleotides thereon. In some flow cells, the polynucleotides in the colony have the same sequence, being for example, clonal copies of a single stranded or double stranded template. However, in some flow cells a reaction site may contain only a single polynucleotide molecule, for example, in a single stranded or double stranded form.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

To read the machine-written DNA, one or more discrete detectable regions of reaction sites may be defined. Such detectable regions may be imagable regions, electrical detection regions, or other types of regions that may have a measurable change in a property (or absence of change in the property) based on the type of nucleotide present during the reading process.

As used herein, the term "pixel" refers to a discrete imagable region. Each imagable region may include a compartment or discrete region of space where a polynucleotide is present. In some instances, a pixel may include two or more reaction sites (e.g., two or more reaction chambers, two or more reaction recesses, two or more wells, etc.). In some other instances, a pixel may include just one reaction site. Each pixel is detected using a corresponding detection device, such as an image sensor or other light detection device. The light detection device may be manufactured using integrated circuit manufacturing processes, such as processes used to manufacture charged-coupled devices circuits (CCD) or complementary-metal-oxide semiconductor (CMOS) devices or circuits. The light detection device may thereby include, for example, one or more semiconductor materials, and may take the form of, for example, a CMOS light detection device (e.g., a CMOS image sensor) or a CCD image sensor, another type of image sensor. A CMOS image sensor may include an array of light sensors (e.g. photodiodes). In one implementation, a single image sensor may be used with an objective lens to capture several "pixels," during an imaging event. In some other implementations, each discrete photodiode or light sensor may capture a corresponding pixel. In some implementations, light sensors (e.g., photodiodes) of one or more detection devices may be associated with corresponding reaction sites. A light sensor that is associated with a reaction site may detect light emissions from the associated reaction site. In some implementations, the detection of light emissions may be done via at least one light guide when a designated reaction has occurred at the associated reaction site. In some implementations, a plurality of light sensors (e.g., several pixels of a light detection or camera device) may be associated with a single reaction site. In some implementations, a single light sensor (e.g. a single pixel) may be associated with a single reaction site or with a group of reaction sites.

As used herein, the term "synthesis" shall be read to include processes where DNA is generated by a machine to store data or other information. Thus, machine-written DNA may constitute synthesized DNA. As used herein, the terms "consumable cartridge," "reagent cartridge," "removeable cartridge," and/or "cartridge" refer to the same cartridge and/or a combination of components making an assembly for a cartridge or cartridge system. The cartridges described herein may be independent of the element with the reaction sites, such as a flow cell having a plurality of wells. In some instances, a flow cell may be removably inserted into a cartridge, which is then inserted into an instrument. In some other implementations, the flow cell may be removably inserted into the instrument without a cartridge. As used herein, the term "biochemical analysis" may include at least one of biological analysis or chemical analysis.

The term "based on" should be understood to mean that something is determined at least in part by the thing it is indicated as being "based on." To indicate that something must necessarily be completely determined by something else, it is described as being based exclusively on whatever it is completely determined by.

The term "non-nucleotide memory" should be understood to refer to an object, device or combination of devices capable of storing data or instructions in a form other than nucleotides that may be retrieved and/or processed by a device. Examples of "non-nucleotide memory" include solid state memory, magnetic memory, hard drives, optical drives and combinations of the foregoing (e.g., magneto-optical storage elements).

The term "DNA storage device" should be understood to refer to an object, device, or combination of devices configured to store data or instructions in the form of sequences of polynucleotides such as machine-written DNA. Examples of "DNA storage devices" include flow cells having addressable wells as described herein, systems comprising multiple such flow cells, and tubes or other containers storing nucleotide sequences that have been cleaved from the surface on which they were synthesized. As used herein, the term "nucleotide sequence" or "polynucleotide sequence" should be read to include a polynucleotide molecule, as well as the underlying sequence of the molecule, depending on context. A sequence of a polynucleotide may contain (or encode) information indicative of certain physical characteristics.

Implementations set forth herein may be used to perform designated reactions for consumable cartridge preparation and/or biochemical analysis and/or synthesis of machine-written DNA.

I. System Overview

FIG. 1 is a schematic diagram of a system 100 that is configured to conduct biochemical analysis and/or synthesis. The system 100 may include a base instrument 102 that is configured to receive and separably engage a removable cartridge 200 and/or a component with one or more reaction sites. The base instrument 102 and the removable cartridge 200 may be configured to interact with each other to transport a biological material to different locations within the system 100 and/or to conduct designated reactions that include the biological material in order to prepare the biological material for subsequent analysis (e.g., by synthesizing the biological material), and, optionally, to detect one or more events with the biological material. In some implementations, the base instrument 102 may be configured to detect one or more events with the biological material directly on the removable cartridge 200. The events may be indicative of a designated reaction with the biological material. The removable cartridge 200 may be constructed according to any of the cartridges described herein.

Although the following is with reference to the base instrument 102 and the removable cartridge 200 as shown in FIG. 1, it is understood that the base instrument 102 and the removable cartridge 200 illustrate only one implementation of the system 100 and that other implementations exist. For example, the base instrument 102 and the removable cartridge 200 include various components and features that, collectively, execute several operations for preparing the biological material and/or analyzing the biological material. Moreover, although the removable cartridge 200 described herein includes an element with the reaction sites, such as a flow cell having a plurality of wells, other cartridges may be independent of the element with the reaction sites and the element with the reaction sites may be separately insertable into the base instrument 102. That is, in some instances a flow cell may be removably inserted into the removable cartridge 200, which is then inserted into the base instrument 102. In some other implementations, the flow cell may be removably inserted directly into the base instrument 102 without the removable cartridge 200. In still further implementations, the flow cell may be integrated into the removable cartridge 200 that is inserted into the base instrument 102.

In the illustrated implementation, each of the base instrument 102 and the removable cartridge 200 are capable of performing certain functions. It is understood, however, that the base instrument 102 and the removable cartridge 200 may perform different functions and/or may share such functions. For example, the base instrument 102 is shown to include a detection assembly 110 (e.g., an imaging device) that is configured to detect the designated reactions at the removable cartridge 200. In alternative implementations, the removable cartridge 200 may include the detection assembly and may be communicatively coupled to one or more components of the base instrument 102. As another example, the base instrument 102 is a "dry" instrument that does not provide, receive, or exchange liquids with the removable cartridge 200. That is, as shown, the removable cartridge 200 includes a consumable reagent portion 210 and a flow cell receiving portion 220. The consumable reagent portion 210 may contain reagents used during biochemical analysis and/or synthesis. The flow cell receiving portion 220 may include an optically transparent region or other detectible region for the detection assembly 110 to perform detection of one or more events occurring within the flow cell receiving portion 220. In alternative implementations, the base instrument 102 may provide, for example, reagents or other liquids to the removable cartridge 200 that are subsequently consumed (e.g., used in designated reactions or synthesis procedures) by the removable cartridge 200.

As used herein, the biological material may include one or more biological or chemical substances, such as nucleosides, nucleotides, nucleic acids, polynucleotides, oligonucleotides, proteins, enzymes, peptides, oligopeptides, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological material may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, viruses including viral pathogens, liquids containing multi-celled organisms, biological swabs and biological washes. In some instances, the biological material may include a set of synthetic sequences, including but not limited to machine-written DNA, which may be fixed (e.g., attached in specific wells in a cartridge) or unfixed (e.g., stored in a tube).

In some implementations, the biological material may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological material. In other aspects, the added material may be a carrier for the biological material such as cell culture media or other buffered and/or pH adjusted and/or isotonic carrier that may allow for or preserve the biological function of the biological material.

It should be understood, however, that the biological material that is analyzed may be in a different form or state than the biological material loaded into or created by the system 100. For example, a biological material loaded into the system 100 may include whole blood or saliva or cell population that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological material" is used while describing a first operation, such as PCR, and used again while describing a subsequent second operation, such as sequencing, it is understood that the biological material in the second operation may be modified with respect to the biological material prior to or during the first operation. For example, sequencing (e.g. SBS) may be carried out on amplicon nucleic acids that are produced from template nucleic acids that are amplified in a prior amplification (e.g. PCR). In this case the amplicons are copies of the templates and the amplicons are present in higher quantity compared to the quantity of the templates.

In some implementations, the system 100 may automatically prepare a sample for biochemical analysis based on a substance provided by the user (e.g., whole blood or saliva or a population of cells). However, in other implementations, the system 100 may analyze biological materials that are partially or preliminarily prepared for analysis by the user. For example, the user may provide a solution including nucleic acids that were already isolated and/or amplified from whole blood; or may provide a virus sample in which the RNA or DNA sequence is partially or wholly exposed for processing.

As used herein, a "designated reaction" includes a change in at least one of a chemical, electrical, physical, or optical property (or quality) of an analyte-of-interest. In particular implementations, the designated reaction is an associative binding event (e.g., incorporation of a fluorescently labeled biomolecule with the analyte-of-interest). The designated reaction may be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Some reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction may also be addition or removal of a proton, for example, detectable as a change in pH of a surrounding solution or environment. An additional designated reaction may be detecting the flow of ions across a membrane (e.g., natural or synthetic bilayer membrane). For example, as ions flow through a membrane, the current is disrupted, and the disruption may be detected. Field sensing of charged tags may also be used; as may thermal sensing and other suitable analytical sensing techniques.

In particular implementations, the designated reaction includes the incorporation of a fluorescently labeled molecule to an analyte. The analyte may be an oligonucleotide and the fluorescently labeled molecule may be a nucleotide. The designated reaction may be detected when an excitation light is directed toward the oligonucleotide having the labeled nucleotide, and the fluorophore emits a detectable fluorescent signal. In alternative implementations, the detected fluorescence is a result of chemiluminescence and/or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological material is immobilized. The reaction components may interact directly or indirectly with the biological material. In some implementations, the removable cartridge 200 is preloaded with one or more of the reaction components involved in carrying out a designated assay protocol. Preloading may occur at one location (e.g. a manufacturing facility) prior to receipt of the cartridge 200 by a user (e.g. at a customer's facility). For example, the one or more reaction components or reagents may be preloaded into the consumable reagent portion 210. In some implementations, the removable cartridge 200 may also be preloaded with a flow cell in the flow cell receiving portion 220.

In some implementations, the base instrument 102 may be configured to interact with one removable cartridge 200 per session. After the session, the removable cartridge 200 may be replaced with another removable cartridge 200. In other implementations, the base instrument 102 may be configured to interact with more than one removable cartridge 200 per session. As used herein, the term "session" includes performing at least one of sample preparation and/or biochemical analysis protocol. Sample preparation may include synthesizing the biological material; and/or separating, isolating, modifying, and/or amplifying one or more components of the biological material so that the prepared biological material is suitable for analysis. In some implementations, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 200 and the base instrument 102 may include the components for executing the different operations. The operations of an assay protocol may include fluidic operations, thermal-control operations, detection operations, and/or mechanical operations.

A fluidic operation includes controlling the flow of fluid (e.g., liquid or gas) through the system 100, which may be actuated by the base instrument 102 and/or by the removable cartridge 200. In one example, the fluid is in liquid form. For example, a fluidic operation may include controlling a pump to induce flow of the biological material or a reaction component into a reaction chamber.

A thermal-control operation may include controlling a temperature of a designated portion of the system 100, such as one or more portions of the removable cartridge 200. By way of example, a thermal-control operation may include raising or lowering a temperature of a polymerase chain reaction (PCR) zone where a liquid that includes the biological material is stored.

A detection operation may include controlling activation of a detector or monitoring activity of the detector to detect predetermined properties, qualities, or characteristics of the biological material. As one example, the detection operation may include capturing images of a designated area that includes the biological material to detect fluorescent emissions from the designated area. The detection operation may include controlling a light source to illuminate the biological material or controlling a detector to observe the biological material.

A mechanical operation may include controlling a movement or position of a designated component. For example, a mechanical operation may include controlling a motor to move a valve-control component in the base instrument 102 that operably engages a movable valve in the removable cartridge 200. In some cases, a combination of different operations may occur concurrently. For example, the detector may capture images of the reaction chamber as the pump controls the flow of fluid through the reaction chamber. In some cases, different operations directed toward different biological materials may occur concurrently. For instance, a first biological material may be undergoing amplification (e.g., PCR) while a second biological material may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous-based and include polar molecules exhibiting surface tension that holds the liquid together. A liquid may also include non-polar molecules, such as in an oil-based or non-aqueous substance. It is understood that references to a liquid in the present application may include a liquid comprising the combination of two or more liquids. For example, separate reagent solutions may be later combined to conduct designated reactions.

One or more implementations may include retaining the biological material (e.g., template nucleic acid) at a designated location where the biological material is analyzed. As used herein, the term "retained," when used with respect to a biological material, includes attaching the biological material to a surface or confining the biological material within a designated space. As used herein, the term "immobilized," when used with respect to a biological material, includes attaching the biological material to a surface in or on a solid support. Immobilization may include attaching the biological material at a molecular level to the surface. For example, a biological material may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological material to the surface. Immobilizing a biological material to a surface of a substrate may be based upon the properties of the surface of the substrate, the liquid medium carrying the biological material, and the properties of the biological material itself. In some cases, a substrate surface may be functionalized (e.g., chemically or physically modified) to facilitate immobilizing the biological material to the substrate surface. The substrate surface may be first modified to have functional groups bound to the surface. The functional groups may then bind to the biological material to immobilize the biological material thereon. In some cases, a biological material may be immobilized to a surface via a gel.

In some implementations, nucleic acids may be immobilized to a surface and amplified using bridge amplification. Another useful method for amplifying nucleic acids on a surface is rolling circle amplification (RCA), for example, using methods set forth in further detail below. In some implementations, the nucleic acids may be attached to a surface and amplified using one or more primer pairs. For example, one of the primers may be in solution and the other primer may be immobilized on the surface (e.g., 5'-attached). By way of example, a nucleic acid molecule may hybridize to one of the primers on the surface followed by extension of the immobilized primer to produce a first copy of the nucleic acid. The primer in solution then hybridizes to the first copy of the nucleic acid which may be extended using the first copy of the nucleic acid as a template. Optionally, after the first copy of the nucleic acid is produced, the original nucleic acid molecule may hybridize to a second immobilized primer on the surface and may be extended at the same time or after the primer in solution is extended. In any implementation, repeated rounds of extension (e.g., amplification) using the immobilized primer and primer in solution may be used to provide multiple copies of the nucleic acid. In some implementations, the biological material may be confined within a predetermined space with reaction components that are configured to be used during amplification of the biological material (e.g., PCR).

One or more implementations set forth herein may be configured to execute an assay protocol that is or includes an amplification (e.g., PCR) protocol. During the amplification protocol, a temperature of the biological material within a reservoir or channel may be changed in order to amplify a target sequence or the biological material (e.g., DNA of the biological material). By way of example, the biological material may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Implementations may execute multiple amplification cycles. It is noted that the above cycle describes only one particular implementation and that alternative implementations may include modifications to the amplification protocol.

The methods and systems set forth herein may use arrays having features at any of a variety of densities including, for example, at least about 10 features/cm$^2$, about 100 features/cm$^2$, about 500 features/cm$^2$, about 1,000 features/cm$^2$, about 5,000 features/cm$^2$, about 10,000 features/cm$^2$, about 50,000 features/cm$^2$, about 100,000 features/cm$^2$, about 1,000,000 features/cm$^2$, about 5,000,000 features/cm$^2$, or higher. The methods and apparatus set forth herein may include detection components or devices having a resolution that is at least sufficient to resolve individual features at one or more of these densities.

The base instrument 102 may include a user interface 130 that is configured to receive user inputs for conducting a designated assay protocol and/or configured to communicate information to the user regarding the assay. The user interface 130 may be incorporated with the base instrument 102. For example, the user interface 130 may include a touchscreen that is attached to a housing of the base instrument 102 and configured to identify a touch from the user and a location of the touch relative to information displayed on the touchscreen. Alternatively, the user interface 130 may be located remotely with respect to the base instrument 102.

II. Cartridge

The removable cartridge 200 is configured to separably engage or removably couple to the base instrument 102 at a cartridge chamber 140. As used herein, when the terms "separably engaged" or "removably coupled" (or the like) are used to describe a relationship between a removable cartridge 200 and a base instrument 102. The term is intended to mean that a connection between the removable cartridge 200 and the base instrument 102 are separable without destroying the base instrument 102. Accordingly, the removable cartridge 200 may be separably engaged to the base instrument 102 in an electrical manner such that the electrical contacts of the base instrument 102 are not destroyed. The removable cartridge 200 may be separably engaged to the base instrument 102 in a mechanical manner such that features of the base instrument 102 that hold the removable cartridge 200, such as the cartridge chamber 140, are not destroyed. The removable cartridge 200 may be separably engaged to the base instrument 102 in a fluidic manner such that the ports of the base instrument 102 are not destroyed. The base instrument 102 is not considered to be "destroyed," for example, if only a simple adjustment to the component (e.g., realigning) or a simple replacement (e.g., replacing a nozzle) is required. Components (e.g., the removable cartridge 200 and the base instrument 102) may be readily separable when the components may be separated from each other without undue effort or a significant amount of time spent in separating the components. In some implementations, the removable cartridge 200 and the base instrument 102 may be readily separable without destroying either the removable cartridge 200 or the base instrument 102.

In some implementations, the removable cartridge 200 may be permanently modified or partially damaged during a session with the base instrument 102. For instance, containers holding liquids may include foil covers that are pierced to permit the liquid to flow through the system 100. In such implementations, the foil covers may be damaged such that the damaged container is to be replaced with another container. In particular implementations, the removable cartridge 200 is a disposable cartridge such that the removable cartridge 200 may be replaced and optionally disposed after a single use. Similarly, a flow cell of the removable cartridge 200 may be separately disposable such that the flow cell may be replaced and optionally disposed after a single use.

In other implementations, the removable cartridge 200 may be used for more than one session while engaged with the base instrument 102 and/or may be removed from the base instrument 102, reloaded with reagents, and re-engaged to the base instrument 102 to conduct additional designated reactions. Accordingly, the removable cartridge 200 may be refurbished in some cases such that the same removable cartridge 200 may be used with different consumables (e.g., reaction components and biological materials). Refurbishing may be carried out at a manufacturing facility after the cartridge 200 has been removed from a base instrument 102 located at a customer's facility.

The cartridge chamber 140 may include a slot, mount, connector interface, and/or any other feature to receive the removable cartridge 200 or a portion thereof to interact with the base instrument 102.

The removable cartridge 200 may include a fluidic network that may hold and direct fluids (e.g., liquids or gases) therethrough. The fluidic network may include a plurality of interconnected fluidic elements that are capable of storing a fluid and/or permitting a fluid to flow therethrough. Non-limiting examples of fluidic elements include channels, ports of the channels, cavities, storage devices, reservoirs of the storage devices, reaction chambers, waste reservoirs, detection chambers, multipurpose chambers for reaction and detection, and the like. For example, the consumable reagent portion 210 may include one or more reagent wells or chambers storing reagents and may be part of or coupled to the fluidic network. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some implementations, it may not be possible to direct the fluid in the channel back to the assay reservoir. In particular implementations, the fluidic network may be configured to receive a biological material and direct the biological material through sample preparation and/or sample analysis. The fluidic network may direct the biological material and other reaction components to a waste reservoir.

Figure 2:
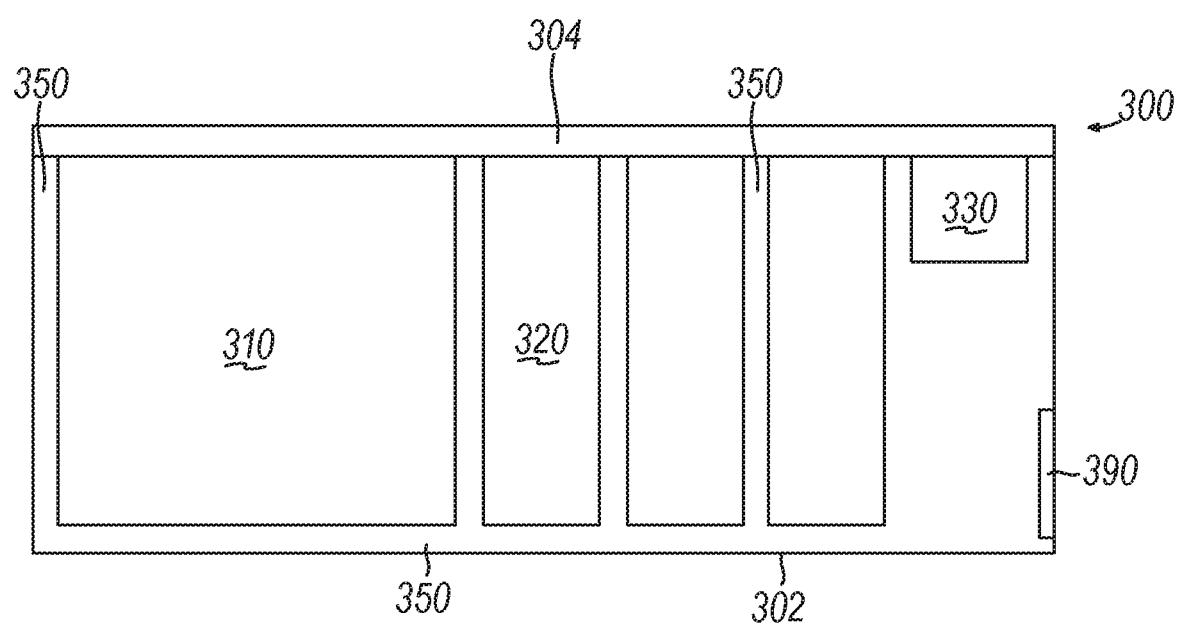
FIG. 2 depicts a block schematic cross-sectional view of an example of a consumable cartridge that may be utilized with the system of FIG. 1.

FIG. 2 depicts an implementation of a consumable cartridge 300. The consumable cartridge may be part of a combined removable cartridge, such as consumable reagent portion 210 of removable cartridge 200 of FIG. 1; or may be a separate reagent cartridge. The consumable cartridge 300 may include a housing 302 and a top 304. The housing 302 may comprise a non-conductive polymer or other material and be formed to make one or more reagent chambers 310, 320, 330. The reagent chambers 310, 320, 330 may be varying in size to accommodate varying volumes of reagents to be stored therein. For instance, a first chamber 310 may be larger than a second chamber 320, and the second chamber 320 may be larger than a third chamber 330. The first chamber 310 is sized to accommodate a larger volume of a particular reagent, such as a buffer reagent. The second chamber 320 may be sized to accommodate a smaller volume of reagent than the first chamber 310, such as a reagent chamber holding a cleaving reagent. The third chamber 330 may be sized to accommodate an even smaller volume of reagent than the first chamber 310 and the second chamber 320, such as a reagent chamber holding a fully functional nucleotide containing reagent.

In the illustrated implementation, the housing 302 has a plurality of housing walls or sides 350 forming the chambers 310, 320, 330 therein. In the illustrated implementation, the housing 302 forms a structure that is at least substantially unitary or monolithic. In alternative implementations, the housing 302 may be constructed by one or more subcomponents that are combined to form the housing 302, such as independently formed compartments for chambers 310, 320, and 330.

The housing 302 may be sealed by the top 304 once reagents are provided into the respective chambers 310, 320, 330. The top 304 may comprise a conductive or non-conductive material. For instance, the top 304 may be an aluminum foil seal that is adhesively coupled to top surfaces of the housing 302 to seal the reagents within their respective chambers 310, 320, 330. In other implementations, the top 304 may be a plastic seal that is adhesively coupled to top surfaces of the housing 302 to seal the reagents within their respective chambers 310, 320, 330.

In some implementations, the housing 302 may also include an identifier 390. The identifier 390 may be a radio-frequency identification (RFID) transponder, a barcode, an identification chip, and/or other identifier. In some implementations, the identifier 390 may be embedded in the housing 302 or attached to an exterior surface. The identifier 390 may include data for a unique identifier for the consumable cartridge 300 and/or data for a type of the consumable cartridge 300. The data of the identifier 390 may be read by the base instrument 102 or a separate device configured for warming the consumable cartridge 300, as described herein.

In some implementations, the consumable cartridge 300 may include other components, such as valves, pumps, fluidic lines, ports, etc. In some implementations, the consumable cartridge 300 may be contained within a further exterior housing.

III. System Controller

The base instrument 102 may also include a system controller 120 that is configured to control operation of at least one of the removable cartridge 200 and/or the detection assembly 110. The system controller 120 may be implemented utilizing any combination of dedicated hardware circuitry, boards, DSPs, processors, etc. Alternatively, the system controller 120 may be implemented utilizing an off-the-shelf PC with a single processor or multiple processors, with the functional operations distributed between the processors. As a further option, the system controller 120 may be implemented utilizing a hybrid configuration in which certain modular functions are performed utilizing dedicated hardware, while the remaining modular functions are performed utilizing an off-the-shelf PC and the like.

The system controller 120 may include a plurality of circuitry modules that are configured to control operation of certain components of the base instrument 102 and/or the removable cartridge 200. The term "module" herein may refer to a hardware device configured to perform specific task(s). For instance, the circuitry modules may include a flow-control module that is configured to control flow of fluids through the fluidic network of the removable cartridge 200. The flow-control module may be operably coupled to valve actuators and/or s system pump. The flow-control module may selectively activate the valve actuators and/or the system pump to induce flow of fluid through one or more paths and/or to block flow of fluid through one or more paths.

The system controller 120 may also include a thermal-control module. The thermal-control module may control a thermocycler or other thermal component to provide and/or remove thermal energy from a sample-preparation region of the removable cartridge 200 and/or any other region of the removeable cartridge 200. In one particular example, a thermocycler may increase and/or decrease a temperature that is experienced by the biological material in accordance with a PCR protocol.

The system controller 120 may also include a detection module that is configured to control the detection assembly 110 to obtain data regarding the biological material. The detection module may control operation of the detection assembly 110 either through a direct wired connection or through the contact array if the detection assembly 110 is part of the removable cartridge 200. The detection module may control the detection assembly 110 to obtain data at predetermined times or for predetermined time periods. By way of example, the detection module may control the detection assembly 110 to capture an image of a reaction chamber of the flow cell receiving portion 220 of the removable cartridge when the biological material has a fluorophore attached thereto. In some implementations, a plurality of images may be obtained.

Optionally, the system controller 120 may include an analysis module that is configured to analyze the data to provide at least partial results to a user of the system 100. For example, the analysis module may analyze the imaging data provided by the detection assembly 110. The analysis may include identifying a sequence of nucleic acids of the biological material.

The system controller 120 and/or the circuitry modules described above may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an implementation, the system controller 120 and/or the circuitry modules execute a set of instructions that are stored in a computer- or machine-readable medium therein in order to perform one or more assay protocols and/or other operations. The set of instructions may be stored in the form of information sources or physical memory elements within the base instrument 102 and/or the removable cartridge 200. The protocols performed by the system 100 may be used to carry out, for example, machine-writing DNA or otherwise synthesizing DNA (e.g., converting binary data into a DNA sequence and then synthesizing DNA strands or other polynucleotides representing the binary data), quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various implementations described herein. The set of instructions may be in the form of a software program. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are only examples and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 120 may be connected to the other components or sub-systems of the system 100 via communication links, which may be hardwired or wireless. The system controller 120 may also be communicatively connected to off-site systems or servers. The system controller 120 may receive user inputs or commands, from a user interface 130. The user interface 130 may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the system 100 at different locations. In some implementations, one or more components may be integrated with the base instrument 102 and one or more components may be located remotely with respect to the base instrument 102.

IV. Flow Cell

Figure 3:
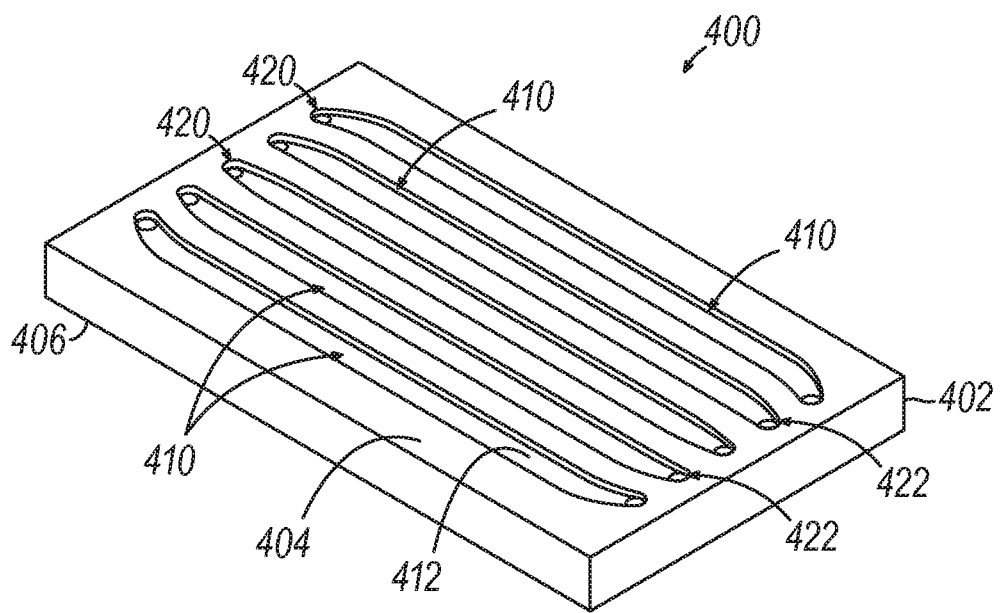
FIG. 3 depicts a perspective view of an example of a flow cell that may be utilized with the system of FIG. 1.
Figure 4:
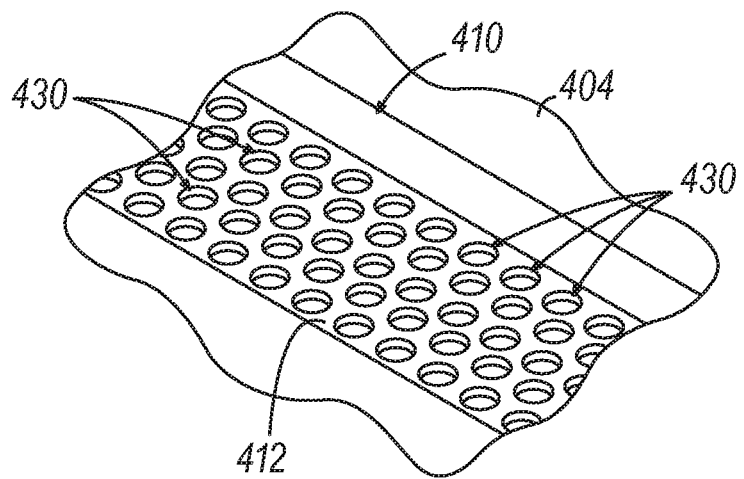
FIG. 4 depicts an enlarged perspective view of a channel of the flow cell of FIG. 3.

FIGS. 3-4 depict an example of a flow cell 400 that may be used with system 100. Flow cell of this example includes a body defining a plurality of elongate flow channels 410, which are recessed below an upper surface 404 of the body 402. The flow channels 410 are generally parallel with each other and extend along substantially the entire length of body 402. While five flow channels 410 are shown, a flow cell 400 may include any other suitable number of flow channels 410, including more or fewer than five flow channels 410. The flow cell 400 of this example also includes a set of inlet ports 420 and a set of outlet ports 422, with each port 420, 422 being associated with a corresponding flow channel 410. Thus, each inlet port 420 may be utilized to communicate fluids (e.g., reagents, etc.) to the corresponding channel 410; while each outlet port 422 may be utilized to communicate fluids from the corresponding flow channel 410.

In some versions, the flow cell 400 is directly integrated into the flow cell receiving portion 220 of the removable cartridge 200. In some other versions, the flow cell 400 is removably coupled with the flow cell receiving portion 220 of the removable cartridge 200. In versions where the flow cell 400 is either directly integrated into the flow cell receiving portion 220 or removably coupled with the flow cell receiving portion 220, the flow channels 410 of the flow cell 400 may receive fluids from the consumable reagent portion 210 via the inlet ports 420, which may be fluidly coupled with reagents stored in the consumable reagent portion 210. Of course, the flow channels 410 may be coupled with various other fluid sources or reservoirs, etc., via the ports 420, 422. As another illustrative variation, some versions of consumable cartridge 300 may be configured to removably receive or otherwise integrate the flow cell 400. In such versions, the flow channels 410 of the flow cell 400 may receive fluids from the reagent chambers 310, 320, 330 via the inlet ports 420. Other suitable ways in which the flow cell 400 may be incorporated into the system 100 will be apparent to those skilled in the art in view of the teachings herein.

FIG. 4 shows a flow channel 410 of the flow cell 400 in greater detail. As shown, the flow channel 410 includes a plurality of wells 430 formed in a base surface 412 of the flow channel 410. As will be described in greater detail below each well 430 is configured to contain DNA strands or other polynucleotides, such as machine-written polynucleotides. In some versions, each well 430 has a cylindraceous configuration, with a generally circular cross-sectional profile. In some other versions, each well 430 has a polygonal (e.g., hexagonal, octagonal, etc.) cross-sectional profile. Alternatively, wells 430 may have any other suitable configuration. It should also be understood that wells 430 may be arranged in any suitable pattern, including but not limited to a grid pattern.

Figure 5:
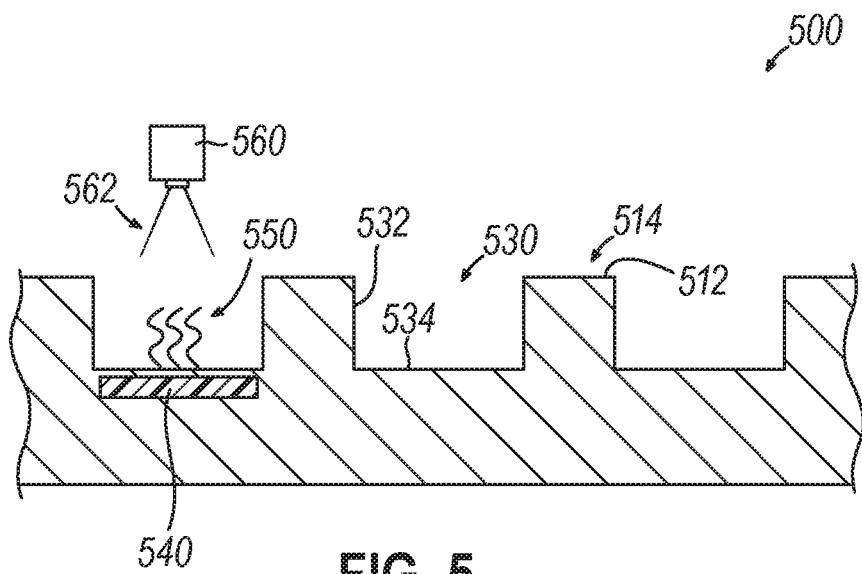
FIG. 5 depicts a block schematic cross-sectional view of an example of wells that may be incorporated into the channel of FIG. 4.

FIG. 5 shows a portion of a channel within a flow cell 500 that is an example of a variation of the flow cell 400. In other words, the channel depicted in FIG. 5 is a variation of the flow channel 410 of the flow cell 400. This flow cell 500 is operable to read polynucleotide strands 550 that are secured to the floor 534 of wells 530 in the flow cell 500. By way of example only, the floor 534 where polynucleotide strands 550 are secured may include a co-block polymer capped with azido. By way of further example only, such a polymer may comprise a poly(N-(5-azidoacetamidylpentyl)acrylamide-co-acrylamide) (PAZAM) coating provided in accordance with at least some of the teachings of U.S. Pat. No. 9,012,022, entitled "Polymer Coatings," issued Apr. 21, 2015, which is incorporated by reference herein in its entirety. Such a polymer may be incorporated into any of the various flow cells described herein.

In the present example, the wells 530 are separated by interstitial spaces 514 provided by the base surface 512 of the flow cell 500. Each well 530 has a sidewall 532 and a floor 534. The flow cell 500 in this example is operable to provide an image sensor 540 under each well 530. In some versions, each well 530 has at least one corresponding image sensor 540, with the image sensors 540 being fixed in position relative to the wells 530. Each image sensor 540 may comprise a CMOS image sensor, a CCD image sensor, or any other suitable kind of image sensor. By way of example only, each well 530 may have one associated image sensor 540 or a plurality of associated image sensors 540. As another variation, a single image sensor 540 may be associated with two or more wells 530. In some versions, one or more image sensors 540 move relative to the wells 530, such that a single image sensor 540 or single group of image sensors 540 may be moved relative to the wells 530. As yet another variation, the flow cell 500 may be movable in relation to the single image sensor 540 or single group of image sensors 540, which may be at least substantially fixed in position.

Each image sensor 540 may be directly incorporated into the flow cell 500. Alternatively, each image sensor 540 may be directly incorporated into a cartridge such as the removable cartridge 200, with the flow cell 500 being integrated into or otherwise coupled with the cartridge. As yet another illustrative variation, each image sensor 540 may be directly incorporated into the base instrument 102 (e.g., as part of the detection assembly 110 noted above). Regardless of where the image sensor(s) 540 is/are located, the image sensor(s) 540 may be integrated into a printed circuit that includes other components (e.g., control circuitry, etc.). In versions where the one or more image sensors 540 are not directly incorporated into the flow cell 500, the flow cell 500 may include optically transmissive features (e.g., windows, etc.) that allow the one or more image sensors 540 to capture fluorescence emitted by the one or more fluorophores associated with the polynucleotide strands 550 that are secured to the floors 534 of the wells 530 in the flow cell 500 as described in greater detail below. It should also be understood that various kinds of optical elements (e.g., lenses, optical waveguides, etc.) may be interposed between the floors 534 of the wells 530 and the corresponding image sensor(s) 540.

As also shown in FIG. 5, a light source 560 is operable to project light 562 into the well 530. In some versions, each well 530 has at least one corresponding light source 560, with the light sources 560 being fixed in position relative to the wells 530. By way of example only, each well 530 may have one associated light source 560 or a plurality of associated light sources 560. As another variation, a single light source 560 may be associated with two or more wells 530. In some other versions, one or more light sources 560 move relative to the wells 530, such that a single light source 560 or single group of light sources 560 may be moved relative to the wells 530. As yet another variation, the flow cell 500 may be movable in relation to the single light source 560 or single group of light sources 560, which may be substantially fixed in position. By way of example only, each light source 560 may include one or more lasers. In another example, the light source 560 may include one or more diodes.

Each light source 560 may be directly incorporated into the flow cell 500. Alternatively, each light source 560 may be directly incorporated into a cartridge such as the removable cartridge 200, with the flow cell 500 being integrated into or otherwise coupled with the cartridge. As yet another illustrative variation, each light source 560 may be directly incorporated into the base instrument 102 (e.g., as part of the detection assembly 110 noted above). In versions where the one or more light sources 560 are not directly incorporated into the flow cell 500, the flow cell 500 may include optically transmissive features (e.g., windows, etc.) that allow the wells 530 to receive the light emitted by the one or more light source 560, to thereby enable the light to reach the polynucleotide strands 550 that are secured to the floor 534 of the wells 530. It should also be understood that various kinds of optical elements (e.g., lenses, optical waveguides, etc.) may be interposed between the wells 530 and the corresponding light source(s) 560.

Figure 6:
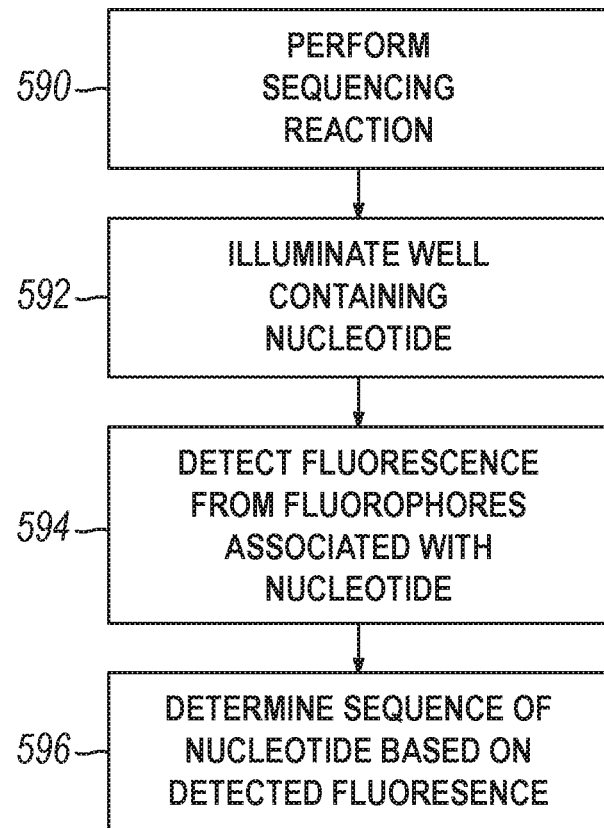
FIG. 6 depicts a flow chart of an example of a process for reading polynucleotides.

As described elsewhere herein and as is shown in block 590 of FIG. 6, a DNA reading process may begin with performing a sequencing reaction in the targeted well(s) 530 (e.g., in accordance with at least some of the teachings of U.S. Pat. No. 9,453,258, entitled "Methods and Compositions for Nucleic Acid Sequencing," issued Sep. 27, 2016, which is incorporated by reference herein in its entirety). Next, as shown in block 592 of FIG. 6, the light source(s) 560 is/are activated over the targeted well(s) 530 to thereby illuminate the targeted well(s) 530. The projected light 562 may cause a fluorophore associated with the polynucleotide strands 550 to fluoresce. Accordingly, as shown in block 594 of FIG. 6, the corresponding image sensor(s) 540 may detect the fluorescence emitted from the one or more fluorophores associated with the polynucleotide strands 550. The system controller 120 of the base instrument 102 may drive the light source(s) 560 to emit the light. The system controller 120 of the base instrument 102 may also process the image data obtained from the image sensor(s) 540, representing the fluorescent emission profiles from the polynucleotide strands 550 in the wells 530. Using this image data from the image sensor(s) 540, and as shown in block 596 of FIG. 6, the system controller 120 may determine the sequence of bases in each polynucleotide strand 550. By way of example only, this process and equipment may be utilized to map a genome or otherwise determine biological information associated with a naturally occurring organism, where DNA strands or other polynucleotides are obtained from or otherwise based on a naturally occurring organism. Alternatively, the above-described process and equipment may be utilized to obtain data stored in machine-written DNA as will be described in greater detail below.

By way of further example only, when carrying out the above-described procedure shown in FIG. 6, time space sequencing reactions may utilize one or more chemistries and imaging events or steps to differentiate between a plurality of analytes (e.g., four nucleotides) that are incorporated into a growing nucleic acid strand during a sequencing reaction; or alternatively, fewer than four different colors may be detected in a mixture having four different nucleotides while still resulting in the determination of the four different nucleotides (e.g., in a sequencing reaction). A pair of nucleotide types may be detected at the same wavelength, but distinguished based on a difference in intensity for one member of the pair compared to the other, or based on a change to one member of the pair (e.g., via chemical modification, photochemical modification, or physical modification) that causes apparent signal to appear or disappear compared to the signal detected for the other member of the pair.

V. Machine-Writing Biological Material

In some implementations, a system 100 such as the system 100 shown in FIG. 1 may be configured to synthesize biological materials (e.g. polynucleotide, such as DNA) to encode data that may later be retrieved through the performance of assays such as those described above. In some implementations, this type of encoding may be performed by assigning values to nucleotide bases (e.g., binary values, such as 0 or 1, ternary values such as 0, 1 or 2, etc.), converting the data to be encoded into a string of the relevant values (e.g., converting a textual message into a binary string using the ASCII encoding scheme), and then creating one or more polynucleotides made up of nucleotides having bases in a sequence corresponding to the string obtained by converting the data.

Figure 7:
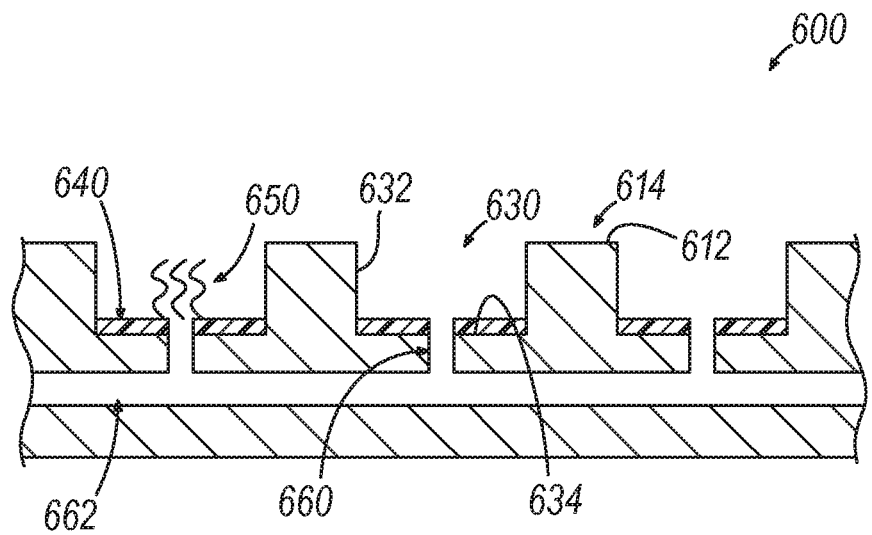
FIG. 7 depicts a block schematic cross-sectional view of another example of wells that may be incorporated into the channel of FIG. 4.

In some implementations, the creation of such polynucleotides may be performed using a version of the flow cell 400 having an array of wells 630 that are configured as shown in FIG. 7. FIG. 7 shows a portion of a channel within a flow cell 600 that is an example of a variation of the flow cell 400. In other words, the channel depicted in FIG. 7 is a variation of the flow channel 410 of the flow cell 400. In this example, each well 630 is recessed below a base surface 612 of the flow cell 600. The wells 630 are thus spaced apart from each other by interstitial spaces 614. By way of example only, the wells 630 may be arranged in a grid or any other suitable pattern along the base surface 612 of the flow cell 600. Each well 630 of this example includes a sidewall 632 and a floor 634. Each well 630 of this example further includes a respective electrode assembly 640 positioned on the floor 634 of the well 630. In some versions, each electrode assembly 640 includes just a single electrode element. In some other versions, each electrode assembly 640 includes a plurality of electrode elements or segments. The terms "electrode" and "electrode assembly" should be read herein as being interchangeable.

Base instrument 102 is operable to independently activate electrode assemblies 640, such that one or more electrode assemblies 640 may be in an activated state while one or more other electrode assemblies 640 are not in an activated state. In some versions, a CMOS device or other device is used to control electrode assemblies 640. Such a CMOS device may be integrated directly into the flow cell 600, may be integrated into a cartridge (e.g., cartridge 200) in which the flow cell 600 is incorporated, or may be integrated directly into the base instrument 102. As shown in FIG. 7, each electrode assembly 640 extends along the full width of floor 634, terminating at the sidewall 632 of the corresponding well 630. In other versions, each electrode assembly 640 may extend along only a portion of the floor 634. For instance, some versions of electrode assembly 640 may terminate interiorly relative to the sidewall 632. While each electrode assembly 540 is schematically depicted as a single element in FIG. 5, it should be understood that each electrode assembly 540 may in fact be formed by a plurality of discrete electrodes rather than just consisting of one single electrode.

As shown in FIG. 7, specific polynucleotide strands 650 may be created in individual wells 630 by activating the electrode assembly 640 of the relevant wells 630 to electrochemically generate acid that may deprotect the end group of the polynucleotide strand 650 in the well 630. By way of example only, polynucleotide strands 650 may be chemically attached to the surface at the bottom of the well 630 using linkers having chemistries such as silane chemistry on one end and DNA synthesis compatible chemistry (e.g., a short oligo for enzyme to bind to) on the other end.

To facilitate reagent exchange (e.g., transmission of a deblocking agent), each electrode assembly 640 and the floor 634 of each well 630 may include at least one opening 660 in this example. The openings 660 may be fluidly coupled with a flow channel 662 that extends underneath the wells 630, below the floors 634. To provide such an opening 660 through the electrode assembly 640, the electrode assembly 640 may be annular in shape, may be placed in quadrants, may be placed on the perimeter or sidewall 632 of the well 630, or may be placed or shaped in other suitable manners to avoid interference with reagent exchange and/or passage of light (e.g., as may be used in a sequencing process that involved detection of fluorescent emissions). In other implementations, reagents may be provided into the flow channel of the flow cell 600 without the openings 660. It should be understood that the openings 660 may be optional and may be omitted in some versions. Similarly, the flow channel 662 may be optional and may be omitted in some versions.

Figure 9:
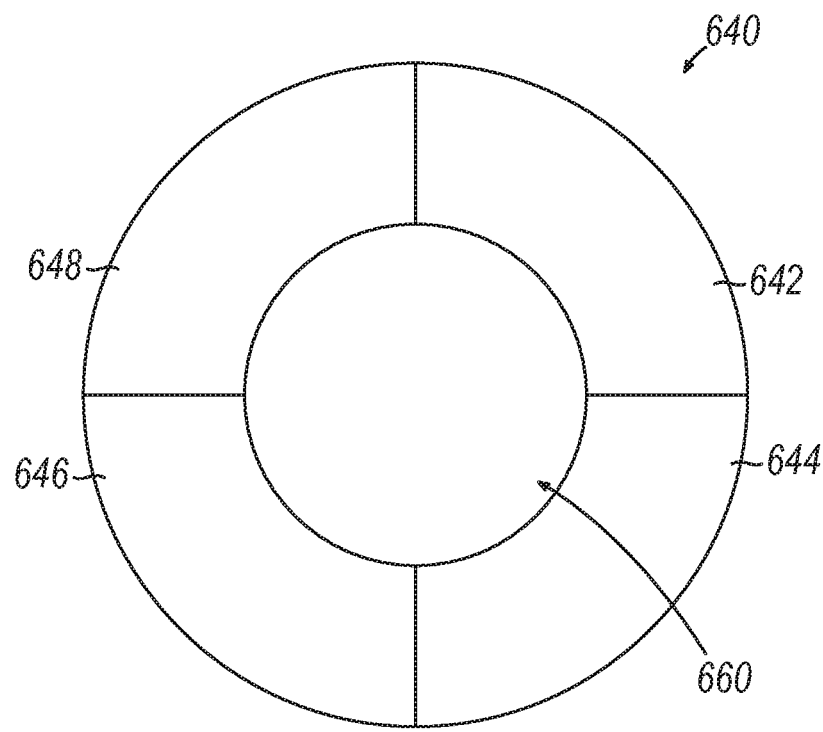
FIG. 9 depicts a top plan view of an example of an electrode assembly.

FIG. 9 shows an example of a form that electrode assembly 640 may take. In this example, electrode assembly 640 includes four discrete electrode segments 642, 644, 646, 648 that together define an annular shape. The electrode segments 642, 644, 646, 648 are thus configured as discrete yet adjacent quadrants of a ring. Each electrode segment 642, 644, 646, 648 may be configured to provide a predetermined charge that is uniquely associated with a particular nucleotide. For instance, electrode segment 642 may be configured to provide a charge that is uniquely associated with adenine; electrode segment 644 may be configured to provide a charge that is uniquely associated with cytosine; electrode segment 646 may be configured to provide a charge that is uniquely associated with guanine; and electrode segment 648 may be configured to provide a charge that is uniquely associated with thymine. When a mixture of those four nucleotides are flowed through the flow channel above the wells 630, activation of electrode segments 642, 644, 646, 648 may cause the corresponding nucleotides from that flow to adhere to the strand 650. Thus, when electrode segment 642 is activated, it may effect writing of adenine to the strand 650; when electrode segment 644 is activated, it may effect writing of cytosine to the strand 650; when electrode segment 646 is activated, it may effect writing of guanine to the strand 650; and when electrode segment 648 is activated, it may effect writing of thymine to the strand 650. This writing may be provided by the activated electrode segment 642, 644, 646, 648 hybridizing the inhibitor of the enzyme for the pixel associated with the activated electrode segment 642, 644, 646, 648. While electrode segments 642, 644, 646, 648 are shown as forming an annular shape in FIG. 9, it should be understood that any other suitable shape or shapes may be formed by electrode segments 642, 644, 646, 648. In still other implementations, a single electrode may be utilized for the electrode assembly 640 and the charge may be modulated to incorporate various nucleotides to be written to the DNA strand or other polynucleotide.

As another example, the electrode assembly 640 may be activated to provide a localized (e.g., localized within the well 630 in which the electrode assembly 640 is disposed), electrochemically generated change in pH; and/or electrochemically generate a moiety (e.g., a reducing or oxidizing reagent) locally to remove a block from a nucleotide. As yet another variation, different nucleotides may have different blocks; and those blocks may be photocleaved based on a wavelength of light communicated to the well 630 (e.g., light 562 projected from the light source 560). As still another variation, different nucleotides may have different blocks; and those blocks may be cleaved based on certain other conditions. For instance, one of the four blocks may be removed based on a combination of a reducing condition plus either high local pH or low local pH; another of the four blocks may be removed based on a combination of an oxidative condition plus either high local pH or low local pH; another of the four blocks may be removed based on a combination of light and a high local pH; and another of the four blocks may be removed based on a combination of light and a low local pH. Thus, four nucleotides may be incorporated at the same time, but with selective unblocking occurring in response to four different sets of conditions.

The electrode assembly 640 further defines the opening 660 at the center of the arrangement of the electrode segments 642, 644, 646, 648. As noted above, this opening 660 may provide a path for fluid communication between the flow channel 662 and the wells 630, thereby allowing reagents, etc. that are flowed through the flow channel 662 to reach the wells 630. As also noted above, some variations may omit the flow channel 662 and provide communication of reagents, etc. to the wells 630 in some other fashion (e.g., through passive diffusion, etc.). Regardless of whether fluid is communicated through the opening 660, the opening 660 may provide a path for optical transmission through the bottom of the well 630 during a read cycle, as described herein. In some versions, the opening 660 may be optional and may thus be omitted. In versions where the opening 660 is omitted, fluids may be communicated to the wells 630 via one or more flow channels that are above the wells 630 or otherwise positioned in relation to the wells 630. Moreover, the opening 660 may not be needed for providing a path for optical transmission through the bottom of the well 630 during a read cycle. For instance, as described below in relation to the flow cell 601, the electrode assembly 640 may comprise an optically transparent material (e.g., optically transparent conducting film (TCF), etc.), and the flow cell 600 itself may comprise an optically transparent material (e.g., glass), such that the electrode assembly 640 and the material forming the flow cell 600 may allow the fluorescence emitted from the one or more fluorophores associated with the machine-written polynucleotide strands 650 to reach an image sensor 540 that is under the well 630.

Figure 8:
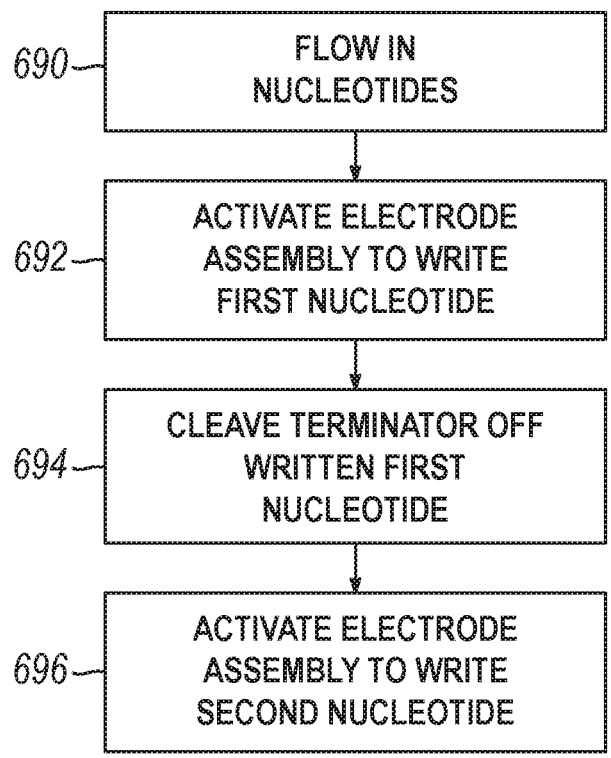
FIG. 8 depicts a flow chart of an example of a process for writing polynucleotides.

FIG. 8 shows an example of a process that may be utilized in the flow cell 600 to machine-write polynucleotides or other nucleotide sequences. At the beginning of the process, as shown in the first block 690 of FIG. 8, nucleotides may be flowed into the flow cell 600, over the wells 630. As shown in the next block 692 in FIG. 8, the electrode assembly 640 may then be activated to write a first nucleotide to a primer at the bottom of a targeted well 630. As shown in the next block 694 of FIG. 8, a terminator may then be cleaved off the first nucleotide that was just written in the targeted well 630. Various suitable ways in which a terminator may be cleaved off the first nucleotide will be apparent to those skilled in the art in view of the teachings herein. Once the terminator is cleaved off the first nucleotide, as shown in the next block 696 of FIG. 8, the electrode assembly 640 may be activated to write a second nucleotide to the first nucleotide. While not shown in FIG. 8, a terminator may be cleaved off the second nucleotide, then a third nucleotide may be written to the second nucleotide, and so on until the desired sequence of nucleotides has been written.

In some implementations, encoding of data via synthesis of biological materials such as DNA may be performed in other manners. For example, in some implementations, the flow cell 600 may lack the electrode assembly 640 altogether. For instance, deblock reagents may be selectively communicated from the flow channel 662 to the wells 630 through the openings 660. This may eliminate the need for electrode assemblies 640 to selectively activate nucleotides. As another example, an array of wells 630 may be exposed to a solution containing all nucleotide bases that may be used in encoding the data, and then individual nucleotides may be selectively activated for individual wells 630 by using light from a spatial light modulator (SLM). As another example, in some implementations individual bases may be assigned combined values (e.g., adenine may be used to encode the binary couplet 00, guanine may be used to encode the binary couplet 01, cytosine may be used to encode the binary couplet 10, and thymine may be used to encode the binary couplet 11) to increase the storage density of the polynucleotides being created. Other examples are also possible and will be immediately apparent to those skilled in the art in light of this disclosure. Accordingly, the above description of synthesizing biological materials such as DNA to encode data should be understood as being illustrative only; and should not be treated as limiting.

VI. Reading Machine-Written Biological Material

After polynucleotide strands 650 have been machine-written in one or more wells 630 of a flow cell 600, the polynucleotide strands 650 may be subsequently read to extract whatever data or other information was stored in the machine-written polynucleotide strands 650. Such a reading process may be carried out using an arrangement such as that shown in FIG. 5 and described above. In other words, one or more light sources 560 may be used to illuminate one or more fluorophores associated with the machine-written polynucleotide strands 650; and one or more image sensors 540 may be used to detect the fluorescent light emitted by the illuminated one or more fluorophores associated with the machine-written polynucleotide strands 650. The fluorescence profile of the light emitted by the illuminated one or more fluorophores associated with the machine-written polynucleotide strands 650 may be processed to determine the sequence of bases in the machine-written polynucleotide strands 650. This determined sequence of bases in the machine-written polynucleotide strands 650 may be processed to determine the data or other information that was stored in the machine-written polynucleotide strands 650.

In some versions, the machine-written polynucleotide strands 650 remain in the flow cell 600 containing wells 630 for a storage period. When it is desired to read the machine-written polynucleotide strands 650, the flow cell 600 may permit the machine-written polynucleotide strands 650 to be read directly from the flow cell. By way of example only, the flow cell 600 containing wells 630 may be received in a cartridge (e.g., cartridge 200) or base instrument 102 containing light sources 560 and/or image sensors 540, such that the machine-written polynucleotide strands 650 are read directly from the wells 630.

Figure 10:
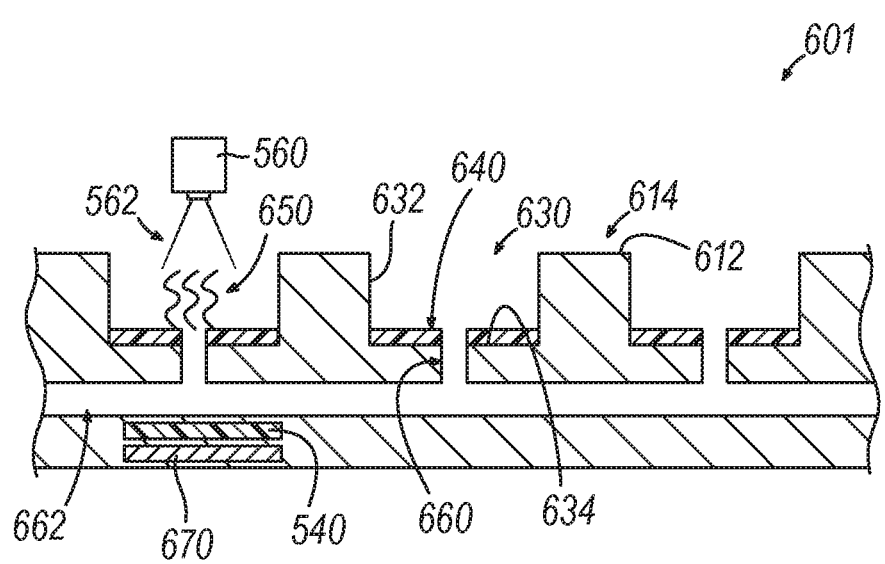
FIG. 10 depicts a block schematic cross-sectional view of another example of wells that may be incorporated into the channel of FIG. 4.

As another illustrative example, the flow cell containing wells 630 may directly incorporate one or both of light source(s) 560 or image sensor(s) 540. FIG. 10 shows an example of a flow cell 601 that includes wells 630 with electrode assemblies 640, one or more image sensors 540, and a control circuit 670. Like in the flow cell 500 depicted in FIG. 5, the flow cell 601 of this example is operable to receive light 562 projected from a light source 560. This projected light 562 may cause one or more fluorophores associated with the machine-written polynucleotide strands 650 to fluoresce; and the corresponding image sensor(s) 540 may capture the fluorescence emitted from the one or more fluorophores associated with the machine-written polynucleotide strands 650.

As noted above in the context of the flow cell 500, each well 650 of the flow cell 601 may include its own image sensor 540 and/or its own light source 560; or these components may be otherwise configured and arranged as described above. In the present example, the fluorescence emitted from the one or more fluorophores associated with the machine-written polynucleotide strands 650 may reach the image sensor 540 via the opening 660. In addition, or in the alternative, the electrode assembly 640 may comprise an optically transparent material (e.g., optically transparent conducting film (TCF), etc.), and the flow cell 601 itself may comprise an optically transparent material (e.g., glass), such that the electrode assembly 640 and the material forming the flow cell 601 may allow the fluorescence emitted from the one or more fluorophores associated with machine-written polynucleotide strands 650 to reach the image sensor 540. Moreover, various kinds of optical elements (e.g., lenses, optical waveguides, etc.) may be interposed between the wells 650 and the corresponding image sensor(s) to ensure that the image sensor 540 is only receiving fluorescence emitted from the one or more fluorophores associated with the machine-written polynucleotide strands 650 of the desired well(s) 630.

In the present example, the control circuit 670 is integrated directly into the flow cell 601. By way of example only, the control circuit 670 may comprise a CMOS chip and/or other printed circuit configurations/components. The control circuit 670 may be in communication with the image sensor(s) 540, the electrode assembly(ies) 640, and/or the light source 560. In this context, "in communication" means that the control circuit 670 is in electrical communication with image sensor(s) 540, the electrode assembly(ies) 640, and/or the light source 560. For instance, the control circuit 670 may be operable to receive and process signals from the image sensor(s) 540, with the signals representing images that are picked up by the image sensor(s) 540. "In communication" in this context may also include the control circuit 670 providing electrical power to the image sensor(s) 540, the electrode assembly(ies) 640, and/or the light source 560.

In some versions, each image sensor 540 has a corresponding control circuit 670. In some other versions, a control circuit 670 is coupled with several, if not all, of the image sensors in the flow cell 601. Various suitable components and configurations that may be used to achieve this will be apparent to those skilled in the art in view of the teachings herein. It should also be understood that the control circuit 670 may be integrated, in whole or in part, in a cartridge (e.g., removable cartridge 200) and/or in the base instrument 102, in addition to or in lieu of being integrated into the flow cell 601.

As still another illustrative example, regardless of whether a write-only flow cell like the flow cell 600 of FIG. 7 or a read-write flow cell like the flow cell 601 of FIG. 10 is used, the machine-written polynucleotide strands 650 may be transferred from wells 630 after being synthesized. This may occur shortly after the synthesis is complete, right before the machine-written polynucleotide strands 650 are to be read, or at any other suitable time. In such versions, the machine-written polynucleotide strands 650 may be transferred to a read-only flow cell like the flow cell 500 depicted in FIG. 5; and then be read in that read-only flow cell 500. Alternatively, any other suitable devices or processes may be used.

In some implementations, reading data encoded through the synthesis of biological materials may be achieved by determining the well(s) 630 storing the synthesized strand(s) 650 of interest and then sequencing those strands 650 using techniques such as those described previously (e.g., sequencing-by-synthesis). In some implementations, to facilitate reading data stored in nucleotide sequences, when data is stored, an index may be updated with information showing the well(s) 630 where the strand(s) 650 encoding that data was/were synthesized. For example, when an implementation of a system 100 configured to synthesize strands 650 capable of storing up to 256 bits of data is used to store a one megabit (1,048,576 bit) file, the system controller 120 may perform steps such as: 1) break the file into 4,096 256 bit segments; 2) identify a sequence of 4,096 wells 630 in the flow cell 600, 601 that were not currently being used to store data; 3) write the 4,096 segments to the 4,096 wells 430, 530; 4) update an index to indicate that the sequence starting with the first identified well 630 and ending at the last identified well 630 was being used to store the file. Subsequently, when a request to read the file was made, the index may be used to identify the well(s) 630 containing the relevant strand(s) 650, the strand(s) 650 from those wells 630 may be sequenced, and the sequences may be combined and converted into the appropriate encoding format (e.g., binary), and that combined and converted data may then be returned as a response to the read request.

In some implementations, reading of data previously encoded via synthesis of biological materials may be performed in other manners. For example, in some implementations, if a file corresponding to 4,096 wells 630 was to be written, rather than identifying 4,096 sequential wells 630 to write it to, a controller may identify 4,096 wells 630 and then update the index with multiple locations corresponding to the file in the event that those wells 630 did not form a continuous sequence. As another example, in some implementations, rather than identifying individual wells 630, a system controller 120 may group wells 630 together (e.g., into groups of 128 wells 630), thereby reducing the overhead associated with storing location data (i.e., by reducing the addressing requirements from one address per well 630 to one address per group of wells 630). As another example, in implementations that store data reflecting the location of wells 630 where DNA strands or other polynucleotides have been synthesized, that data may be stored in various ways, such as sequence identifiers (e.g., well 1, well 2, well 3, etc.) or coordinates (e.g., X and Y coordinates of a well's location in an array).

As another example, in some implementations, rather than reading strands 650 from the wells 630 in which they were synthesized, strands 650 may be read from other locations. For instance, strands 650 may be synthesized to include addresses, and then cleaved from the wells 630 and stored in a tube for later retrieval, during which the included address information may be used to identify the strands 650 corresponding to particular files. As another illustrative example, the strands 650 may be copied off the surface using polymerase and then eluted & stored in tube. Alternatively, the strands 650 may be copied on to a bead using biotinylated oligos hybridized to DNA strands or other polynucleotides and capturing extended products on streptavidin beads that are dispensed in the wells 630. Other examples are also possible and will be immediately apparent to those of skill in the art in light of this disclosure. Accordingly, the above description of retrieving data encoded through the synthesis of biological materials should be understood as being illustrative only; and should not be treated as limiting.

Implementations described herein may utilize a polymer coating for a surface of a flow cell, such as that described in U.S. Pat. No. 9,012,022, entitled "Polymer Coatings," issued Apr. 21, 2015, which is incorporated by reference herein in its entirety. Implementations described herein may utilize one or more labelled nucleotides having a detectable label and a cleavable linker, such as those described in U.S. Pat. No. 7,414,116, entitled "Labelled Nucleotide Strands," issued Aug. 19, 2008, which is incorporated by reference herein in its entirety. For instance, implementations described herein may utilize a cleavable linker that is cleavable with by contact with water-soluble phosphines or water-soluble transition metal-containing catalysts having a fluorophore as a detectable label. Implementations described herein may detect nucleotides of a polynucleotide using a two-channel detection method, such as that described in U.S. Pat. No. 9,453,258, entitled "Methods and Compositions for Nucleic Acid Sequencing," issued Sep. 27, 2016, which is incorporated by reference herein in its entirety. For instance, implementations described herein may utilize a fluorescent-based SBS method having a first nucleotide type detected in a first channel (e.g., dATP having a label that is detected in the first channel when excited by a first excitation wavelength), a second nucleotide type detected in a second channel (e.g., dCTP having a label that is detected in a second channel when excited by a second excitation wavelength), a third nucleotide type detected in both the first and second channel (e.g., dTTP having at least one label that is detected in both channels when excited by the first and/or second excitation wavelength), and a fourth nucleotide type that lacks a label that is not, or that is minimally, detected in either channel (e.g., dGTP having no label). Implementations of the cartridges and/or flow cells described herein may be constructed in accordance with one or more teachings described in U.S. Pat. No. 8,906,320, entitled "Biosensors for Biological or Chemical Analysis and Systems and Methods for Same," issued Dec. 9, 2014, which is incorporated by reference herein in its entirety; U.S. Pat. No. 9,512,422, entitled "Gel Patterned Surfaces," issued Dec. 6, 2016, which is incorporated by reference herein in its entirety; U.S. Pat. No. 10,254,225, entitled "Biosensors for Biological or Chemical Analysis and Methods of Manufacturing the Same," issued Apr. 9, 2019, which is incorporated by reference herein in its entirety; and/or U.S. Pub. No. 2018/0117587, entitled "Cartridge Assembly," published May 3, 2018, which is incorporated by reference herein in its entirety.

VII. Features to Contain Reactions within Wells and Prevent Diffusion Between Wells In a DNA storage device that provides reading and writing capability among various wells 630 of a flow cell 601, it may be beneficial to contain reactions to the wells 630 in which the reactions are intended to occur. In some instances, there may be a risk that the reaction within one well 630 may not be fully contained within that well 630. This may occur during a writing process (e.g., in the case of well 630) or during a reading process (e.g., in the case of well 530, 630). Similarly, it may be beneficial to prevent inter-well diffusion, to thereby prevent the occurrence of chemical cross-talk between adjacent wells 630 in a flow cell 601. Each individual well 601 may incorporate features (e.g., added depth, other features as described below, etc.) that provide such containment and prevent such diffusion. In addition, or in the alternative, the flow cell 601 may include features in the spaces 614 between wells 630 to provide such containment and prevent such diffusion. Several illustrative examples of containment and diffusion prevention features are described in greater detail below. While the following examples are provided separately with reference to separate drawings, it should be understood that the features of the following examples may be combined in numerous ways in the same flow cell. Thus, the containment and diffusion prevention features described below should not be viewed as being exclusive of each other.

A. Flow Cell with Valves in Wells

Figure 11A:
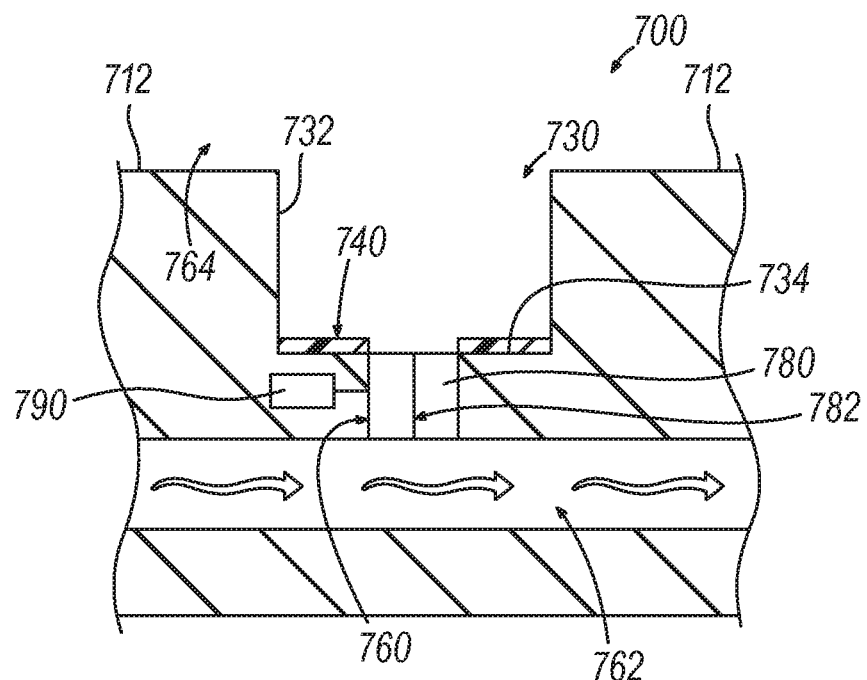
FIG. 11A depicts a block schematic cross-sectional view of another example of a well that may be incorporated into the channel of FIG. 4, with a valve in a closed state.
Figure 11B:
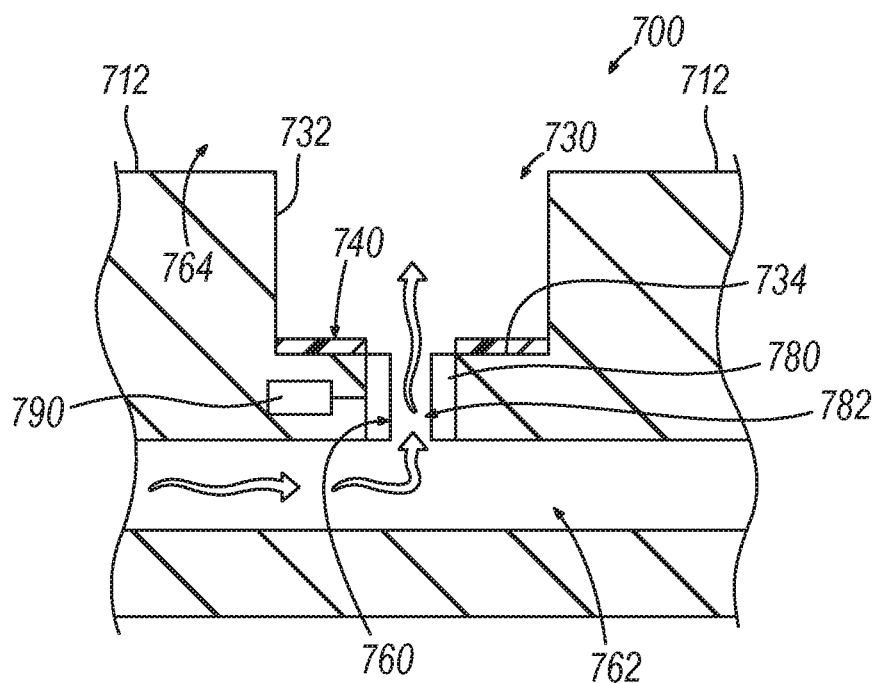
FIG. 11B depicts a block schematic cross-sectional view of the well of FIG. 11A, with the valve in an open state.

FIGS. 11A-11B show an example of a flow cell 700 that may be used to write DNA strands (or other polynucleotides) as described herein. Except as otherwise described below, the flow cell 700 of this example may be configured and operable like the other flow cells 400, 500, 600, 601 described herein. For instance, while an image sensor 540 and a control circuit 670 are not shown in FIGS. 11A-11B, variations of flow cell 700 may in fact include an image sensor 540 and/or a control circuit 670 like the flow cell 601 of FIG. 10. Similarly, the flow cell 700 of this example may incorporate or otherwise be placed under a light source 560 like the flow cell 601 of FIG. 10.

The flow cell 700 of the present example includes a plurality of wells 730 that are recessed below a base surface 712. While only one well 730 is shown in FIGS. 11A-11B, it should be understood that the flow cell 700 may include several wells 730 that are configured just like the depicted well 730; and that the wells 730 may be arranged in any suitable pattern. The flow cell 700 of this example further defines an upper flow channel 764 (e.g., corresponding to the channels 410 shown in FIGS. 3-4), with wells 730 being positioned to receive fluid that is flowed through upper flow channel 764. The flow cell 700 also defines a lower flow channel 762 that is positioned underneath the wells 730. In the present example, the two flow channels 762, 764 are fluidically coupled with different fluid sources. By way of example only, the upper flow channel 764 may be fluidically coupled with one or more fluid sources containing nucleotides; while the lower flow channel 762 may be fluidically coupled with one or more fluid sources containing deblocking agents. Other suitable kinds of fluids, and contents of such fluids, that may be communicated through the respective flow channels 762, 764 will be apparent to those skilled in the art in view of the teachings herein.

Each well 730 of this example includes a sidewall 732 and a floor 734. Each well 730 of this example further includes a respective electrode assembly 740 positioned on the floor 734 of the well 730. In some versions, each electrode assembly 740 includes just a single electrode element. In some other versions, each electrode assembly 740 includes a plurality of electrode elements or segments (e.g., like the electrode segments 642, 644, 646, 648 described above, etc.).

Unlike the flow cell 601 shown in FIG. 10, the flow cell 700 of this example includes a valve 780 that is positioned in an opening 760 extending from the floor 734 of the well 730 to the lower flow channel 762. The valve 780 is in communication with a controller 790 that is operable to drive the valve 780 to transition between a closed state (FIG. 11A) and an open state (FIG. 11B). In some versions, the controller 790 is in electrical communication with the valve 780, such that the controller 790 is operable to provide electrical signals to the valve 780 to thereby activate the valve to thereby transition the valve 780 between open and closed states. When the valve 780 is in the closed state (FIG. 11A), the orifice 782 of the valve is reduced to a point where fluid cannot flow through the orifice 782, such that fluid that flows through the lower flow channel 762 cannot reach the well 730. When the valve 780 is in the open state (FIG. 11B), the orifice 782 of the valve is sized to permit fluid to flow through the orifice 782, such that fluid that flows through the lower flow channel 762 may flow into the well 730.

In some instances, components or techniques are used to provide a pressure differential between the well 730 and the lower flow channel 762 to promote the flow of fluid from the lower flow channel 762 into the well 730 when the valve 780 is in the open state. By way of example only, a pump (not shown), such as an electrokinetic pump or other kind of pump, may be utilized to promote the flow of fluid from the lower flow channel 762 into the well 730 when the valve 780 is in the open state. As another illustrative example, the lower flow channel 762 may include valves or other flow restriction devices between adjacent openings 760 of wells 730 to selectively restrict flow through the lower flow channel 762. For instance, when a valve 780 in a particular opening 760 is in activated to achieve an open state, another valve (not shown) that is downstream of that opening 760 in the lower flow channel 762 may be closed to provide a buildup of pressure in the lower flow channel 762, thereby promoting the flow of fluid from the lower flow channel into the corresponding well 730 via the opened valve 780 in the opening 760 of that well 730. Other suitable components or techniques that may be used to provide a pressure differential between the well 730 and the lower flow channel 762, or to otherwise promote the flow of fluid from the lower flow channel 762 into the well 730 when the valve 780 is in the open state, will be apparent to those skilled in the art in view of the teachings herein.

The controller 790 may take a variety of forms and may drive the valve 780 in numerous different ways, particularly depending on the nature of the valve 780. For instance, some versions of the valve 780 may comprise a hydrogel material that is configured to define a ring shape or hollow cylindraceous shape. In such versions, the hydrogel material may transition between a swelled state or expanded state and a non-swelled state or contracted state to transition the valve 780 between the closed state (FIG. 11A) and the open state FIG. 11B, respectively. The controller 790 may drive the hydrogel material to transition between the swelled state or expanded state and the non-swelled state or contracted state by applying pH changes, reagents, and/or electrical flow. Various suitable ways in which the controller 790 may drive the hydrogel material to transition between the swelled state and the non-swelled state, and various components that may be incorporated into the controller or otherwise associate with the controller 790 to provide such transitioning, will be apparent to those skilled in the art in view of the teachings herein.

As another illustrative example, the valve 780 may comprise a heat swellable polymer. In such versions, the heat swellable polymer may transition between a swelled state and a non-swelled state to transition the valve 780 between the closed state (FIG. 11A) and the open state FIG. 11B, respectively. The controller 790 may drive the heat swellable polymer to transition between the swelled state and the non-swelled state by selectively heating the heat swellable polymer. For instance, the controller 790 may include one or more heating elements that are in thermal communication with the heat swellable polymer, such that the controller 790 may activate the heating elements to thereby cause the heat swellable polymer to swell, thereby causing the valve 780 to close. To open the valve 780, the controller 790 may deactivate the heating elements, and the heat swellable polymer may then cool to the point where the valve 780 reaches a cool state. In some instances, a resilient material is incorporated into valve 780 to resiliently urge the valve 780 to return to the open state when the heating is removed.

Some other versions of the valve 780 may comprise an electroactive polymer. In such versions, the controller 790 may apply a voltage to the valve 780 or remove the voltage from the valve 780 in order to transition the valve 780 between the open and closed states. Other suitable forms that the valve 780 and the controller 790 may take will be apparent to those skilled in the art in view of the teachings herein. While the controller 790 is shown as being positioned adjacent to the valve 780 as a separate unit, such that each valve 780 has separate controllers 790, it should be understood that other versions may provide an integrated circuit that provides control over all valves 780. For instance, a single CMOS chip in the flow cell 700 may be operable to drive all of the valves 780 in the flow cell 700. Even when the controller 790 is effectively embodied in a single device (e.g., a single CMOS chip that controls all of the valves 780 in the flow cell 700), such a unified controller 790 may still operate the valves 780 independently of each other.

Regardless of what form the valve 780 takes, the various valves 780 in the flow cell 700 may be selectively activated to control the flow of fluids from the lower flow channel 762 to the corresponding well(s) 730. For instance, valves 780 may be selectively activated to control the flow of de-shielding/de-blocking agent from the lower flow channel 762 to the corresponding well(s) 730. In other words, closed valves 780 will prevent selected wells 730 from receiving de-shielding/de-blocking agent from the lower flow channel 762, thereby enhancing control over which well 730 provides a reaction at a given moment. Since the valves 780 may be independently operated in the present example, the valves 780 enable the wells 730 to receive de-shielding/de-blocking agent from the lower flow channel 762 independently or in any desired pattern.

B. Flow Cell with Pressure Gradient Feature

Figure 12:
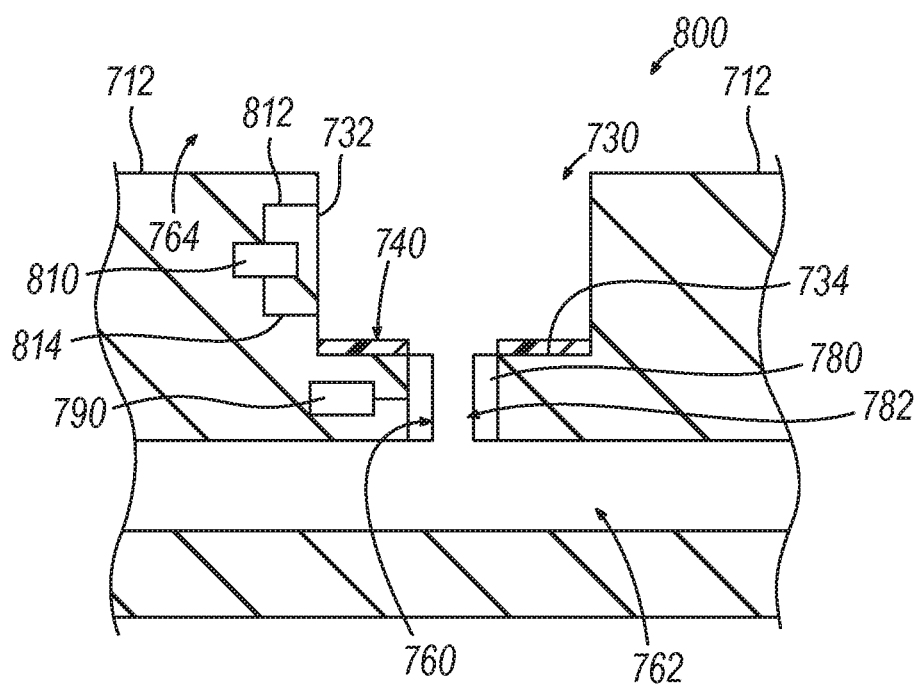
FIG. 12 depicts a block schematic cross-sectional view of another example of a well that may be incorporated into the channel of FIG. 4.

Another way in which a flow cell may provide containment within wells, and prevent diffusion between wells, is to provide a pressure gradient within each well. FIG. 12 shows one illustrative example of how this may be carried out. In particular, FIG. 12 shows a flow cell 800 with a pump assembly 810 having two ports 812, 814. Except for the inclusion of the pump assembly 810 and the ports 812, 814, the flow cell 800 of this example is configured and operable just like the flow cell 700 described above. Thus, like reference numerals indicate like components between the two examples, and these overlapping components will not be further described in the context of this flow cell 800. It should be understood, however, that the pump assembly 810 and the ports 812, 814 may be incorporated into flow cells of different configurations (e.g., a flow cell in which the valve 780 is omitted).

The pump assembly 810 may include an osmotic pump or any other suitable kind of pump. The ports 812, 814 include an upper port 812 and a lower port 814. The ports 812, 814 open into the sidewall 732 of the well 730, such that the ports 812, 814 are fluidically coupled with the well 730. The upper port 812 is positioned near the top of the well 730 and the lower port 814 is positioned near the bottom of the well 730.

The pump assembly 810 is operable to provide a fluid flow or pressure profile that varies across the depth of the well 730. For instance, the pump assembly 810 may provide a fluid flow or pressure profile where the flow or pressure is lower near the bottom of the well 730; with a flow or pressure that is higher near the top of the well 730. In some other variations, the lower port 814 is omitted and the pump assembly 810 draws fluid from the upper flow channel 764 and thereby provides a higher flow or pressure near the top of the well 730 since the lower region of the well is not receiving a flow of fluid directly from the pump assembly 810. In either case, by providing this particular flow or pressure gradient within the well 730, the pump assembly 810 may assist in containing reactions within that well 730; and further prevent diffusion to adjacent wells 730.

The pump assembly 810 may be selectively activated by a controller that is directly integrated into the flow cell 800. By way of example only, such an integrated controller may be incorporated into a CMOS chip. In some such versions, the same CMOS chip or other controller also controls other features of the flow cell 800 (e.g., the valve 780, the electrode assembly 740, etc.). As another illustrative alternative, the pump assembly 810 may be selectively activated by a controller that is directly integrated into a cartridge (e.g., the removable cartridge 200) that receives the flow cell 800. As still another illustrative alternative, the pump assembly 810 may be selectively activated by a controller that is directly integrated into the base instrument 102. Moreover, components of the controller that selectively activates the pump assembly 810 may be distributed among two or more of the flow cell 800, a cartridge that receives the flow cell 800, or the base instrument 102. Various suitable components and arrangements that may be utilized to provide control of the pump assembly 810 will be apparent to those skilled in the art in view of the teachings herein.

Figure 13:
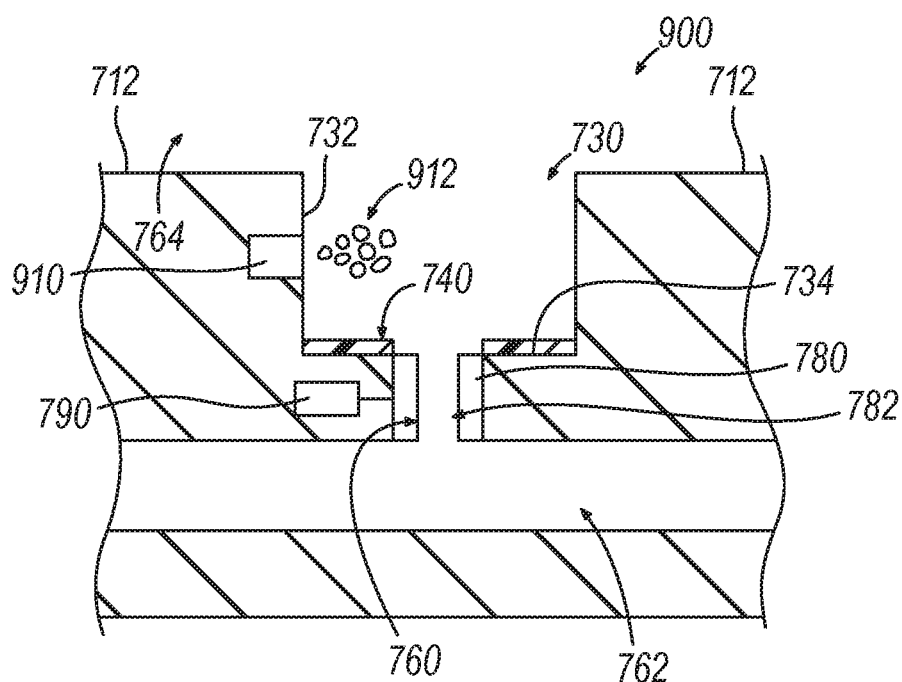
FIG. 13 depicts a block schematic cross-sectional view of another example of a well that may be incorporated into the channel of FIG. 4.

FIG. 13 shows a flow cell 900 with a bubble generator 910. Except for the inclusion of the bubble generator 910, the flow cell 900 of this example is configured and operable just like the flow cell 700 described above. Thus, like reference numerals indicate like components between the two examples, and these overlapping components will not be further described in the context of this flow cell 900. It should be understood, however, that the bubble generator 910 may be incorporated into flow cells of different configurations (e.g., a flow cell in which the valve 780 is omitted, a flow cell like the flow cell 800 of FIG. 12, etc.).

The bubble generator 910 of this example is positioned adjacent to the sidewall 732 of the well 730 and is operable to generate bubbles 910 in the well 730. In the example shown in FIG. 13, the bubble generator 910 is shown as being located in an intermediate position along the depth of the well 730. In other versions, the bubble generator 910 is located near the top of the well 730 or elsewhere. While just one bubble generator 910 is shown, it should be understood that each well 730 may have more than one associated bubble generator 910.

The bubbles 912 that are created by the bubble generator 910 may tend to rise toward the top of the well 730. When the bubbles 912 are produced by the bubble generator 910 in an at least substantially constant stream, the bubbles 912 may effectively prevent liquid that is flowing through the upper flow channel 764 from reaching the well 730 in which the bubbles 912 are being generated. The bubbles 912 may also provide a pressure gradient that effectively contains the reactions that are occurring along the depth of the well 730 between the bubbles 912 and the floor 734 of the well 730. As another illustrative example, the bubble generator 910 may generate a bubble dome over the well 730, thereby separating the well from the rest of the upper flow channel 764. In such versions, the bubble dome may prevent reactions from occurring within that well 730 as long as the bubble dome is present. In any of these variations, by generating bubbles 912, the bubble generator 910 may assist in containing reactions within its associated well 730; and further prevent diffusion to adjacent wells 730.

The bubble generator 910 may be selectively activated by a controller that is directly integrated into the flow cell 900. By way of example only, such an integrated controller may be incorporated into a CMOS chip. In some such versions, the same CMOS chip or other controller also controls other features of the flow cell 900 (e.g., the valve 780, the electrode assembly 740, etc.). As another illustrative alternative, the bubble generator 910 may be selectively activated by a controller that is directly integrated into a cartridge (e.g., the removable cartridge 200) that receives the flow cell 900. As still another illustrative alternative, the bubble generator 910 may be selectively activated by a controller that is directly integrated into the base instrument 102. Moreover, components of the controller that selectively activates the bubble generator 910 may be distributed among two or more of the flow cell 900, a cartridge that receives the flow cell 900, or the base instrument 102. Various suitable components and arrangements that may be utilized to provide control of the bubble generator 910 will be apparent to those skilled in the art in view of the teachings herein.

In any of the foregoing examples, or in other variations of a flow cell 800, 900, a pressure sensitive check valve may also be used to assist in containing reactions within the wells 730 of a flow cell and/or prevent diffusion among wells 730 of the flow cell.

C. Flow Cell with Thermal Gradient Feature

Figure 14:
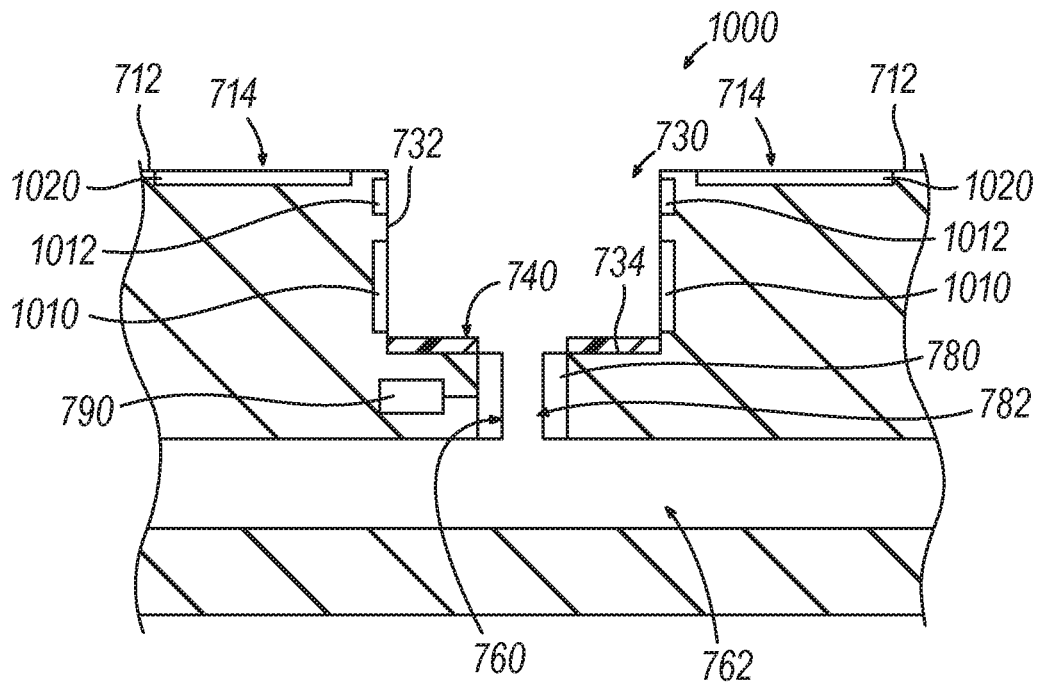
FIG. 14 depicts a block schematic cross-sectional view of another example of a well that may be incorporated into the channel of FIG. 4.

Another way in which a flow cell may provide containment within wells, and prevent diffusion between wells, is to provide a thermal gradient within each well. Sharp thermal gradients may result in thermophoretic gradients of reagents within the well that effectively trap the reagents near an extreme condition (hot or cold). FIG. 14 shows one illustrative example of how thermal gradients may be provided within wells. In particular, FIG. 14 shows a flow cell 1000 with several thermal elements 1010, 1012, 1020 integrated therein. Except for the inclusion of the thermal elements 1010, 1012, 1020, the flow cell 1000 of this example is configured and operable just like the flow cell 700 described above. Thus, like reference numerals indicate like components between the two examples, and these overlapping components will not be further described in the context of this flow cell 1000. It should be understood, however, that the thermal elements 1010, 1012, 1020 may be incorporated into flow cells of different configurations (e.g., a flow cell in which the valve 780 is omitted, a flow cell like the flow cell 800 of FIG. 12, a flow cell like the flow cell 900 of FIG. 13, etc.).

Each thermal element 1010, 1012, 1020 of the present example is operable to either increase or decrease the temperature of liquid that is adjacent to the thermal element 1010, 1012, 1020. The thermal elements 1010 of this example are positioned along the sidewall 732 of the well 730, near the bottom of the well 730. The thermal elements 1012 are positioned along the sidewall 732 of the well 730, near the bottom of the well 730. The thermal elements 1020 are positioned along the base surface 712 of the flow cell 1000, in the interstitial spaces 714 between adjacent wells 730.

The thermal elements 1010 of this example comprise heating elements that are operable to heat the liquid in the bottom region of the well 730. The thermal elements 1012 of this example comprise cryogenic elements that are operable to cool the liquid in the top region of the well 730. The thermal elements 1014 of this example comprise cryogenic elements that are operable to cool the liquid that is adjacent to the interstitial spaces 714 between adjacent wells 730. With the thermal elements 1010 heating the lower region of the well 730, and with the thermal elements 1012 heating the lower region of the well 730, the thermal elements 1010, 1012 cooperate to provide a thermal gradient across the depth of the well 730. This thermal gradient will help contain reactions within the well 730. With the thermal elements 1014 cooling the interstitial spaces 714 between adjacent wells 730, the thermal elements will prevent diffusion from one well 730 to the adjacent well 730.

In some variations, thermal elements 1012 and/or thermal elements 1014 are omitted. While not shown, each thermal element 1010, 1012, 1014 may be selectively activated by a corresponding dedicated controller. Alternatively, a single controller (e.g., CMOS chip) may be utilized to selectively activate the thermal elements 1010, 1012, 1014. In some instances, the entire set of thermal elements 1010, 1012 for a given well 730 is activated independently of the thermal elements 1010, 1012 for other wells 730. As another variation, the thermal elements 1010, 1012 for a given well 730 may be activated independently of each other. It should also be understood that the thermal elements 1014 may be activated independently of the thermal elements 1010, 1012; or in tandem with the thermal elements 1010, 1012.

The thermal elements 1010, 1012, 1014 may be selectively activated by a controller that is directly integrated into the flow cell 1000. By way of example only, such an integrated controller may be incorporated into a CMOS chip. In some such versions, the same CMOS chip or other controller also controls other features of the flow cell 1000 (e.g., the valve 780, the electrode assembly 740, etc.). As another illustrative alternative, the thermal elements 1010, 1012, 1014 may be selectively activated by a controller that is directly integrated into a cartridge (e.g., the removable cartridge 200) that receives the flow cell 1000. As still another illustrative alternative, the thermal elements 1010, 1012, 1014 may be selectively activated by a controller that is directly integrated into the base instrument 102. Moreover, components of the controller that selectively activates the thermal elements 1010, 1012, 1014 may be distributed among two or more of the flow cell 1000, a cartridge that receives the flow cell 1000, or the base instrument 102. Various suitable components and arrangements that may be utilized to provide control of the thermal elements 1010, 1012, 1014 will be apparent to those skilled in the art in view of the teachings herein.

D. Flow Cell with pH Control Feature

Figure 15:
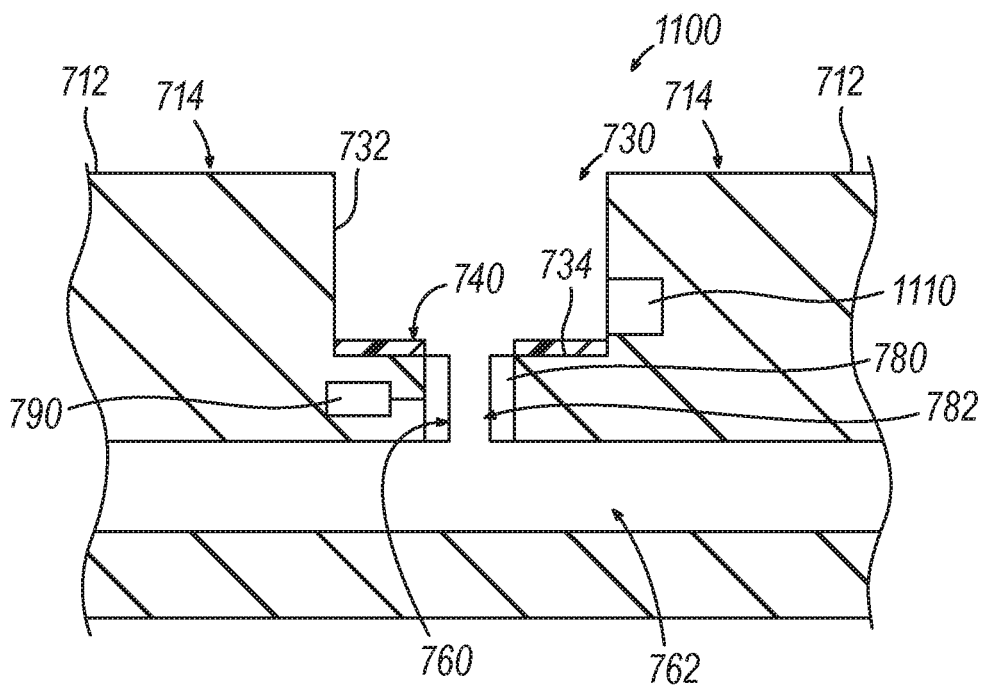
FIG. 15 depicts a block schematic cross-sectional view of another example of a well that may be incorporated into the channel of FIG. 4.

Another way in which a flow cell may prevent diffusion between wells is to provide a pH gradient between adjacent wells. FIG. 15 shows one illustrative example of how this may be carried out. In particular, FIG. 15 shows a flow cell 1100 with a pH control feature 1110 integrated therein. Except for the inclusion of the pH control feature 1110, the flow cell 1100 of this example is configured and operable just like the flow cell 700 described above. Thus, like reference numerals indicate like components between the two examples, and these overlapping components will not be further described in the context of this flow cell 1100. It should be understood, however, that the pH control feature 1110 may be incorporated into flow cells of different configurations (e.g., a flow cell in which the valve 780 is omitted, a flow cell like the flow cell 800 of FIG. 12, a flow cell like the flow cell 900 of FIG. 13, a flow cell like the flow cell 1000 of FIG. 14, etc.).

The pH control feature 1110 of the present example is operable to adjust the pH level within the well 730. By way of example only, the pH control feature may comprise a bubble generator, a set of electrodes, or some other feature. The flow cell 1100 may be configured to one or more pH control features 1110 to provide pH levels that differ among different wells 730. With the pH levels differing between the wells 730, the resulting pH gradient may prevent diffusion between adjacent wells 730.

The pH control feature 1110 may be selectively activated by a controller that is directly integrated into the flow cell 1100. By way of example only, such an integrated controller may be incorporated into a CMOS chip. In some such versions, the same CMOS chip or other controller also controls other features of the flow cell 1100 (e.g., the valve 780, the electrode assembly 740, etc.). As another illustrative alternative, the pH control feature 1110 may be selectively activated by a controller that is directly integrated into a cartridge (e.g., the removable cartridge 200) that receives the flow cell 1100. As still another illustrative alternative, the pH control feature 1110 may be selectively activated by a controller that is directly integrated into the base instrument 102. Moreover, components of the controller that selectively activates the pH control feature 1110 may be distributed among two or more of the flow cell 1100, a cartridge that receives the flow cell 1100, or the base instrument 102. Various suitable components and arrangements that may be utilized to provide control of the pH control feature 1110 will be apparent to those skilled in the art in view of the teachings herein.

E. Flow Cell with Movable Barrier

Figure 16A:
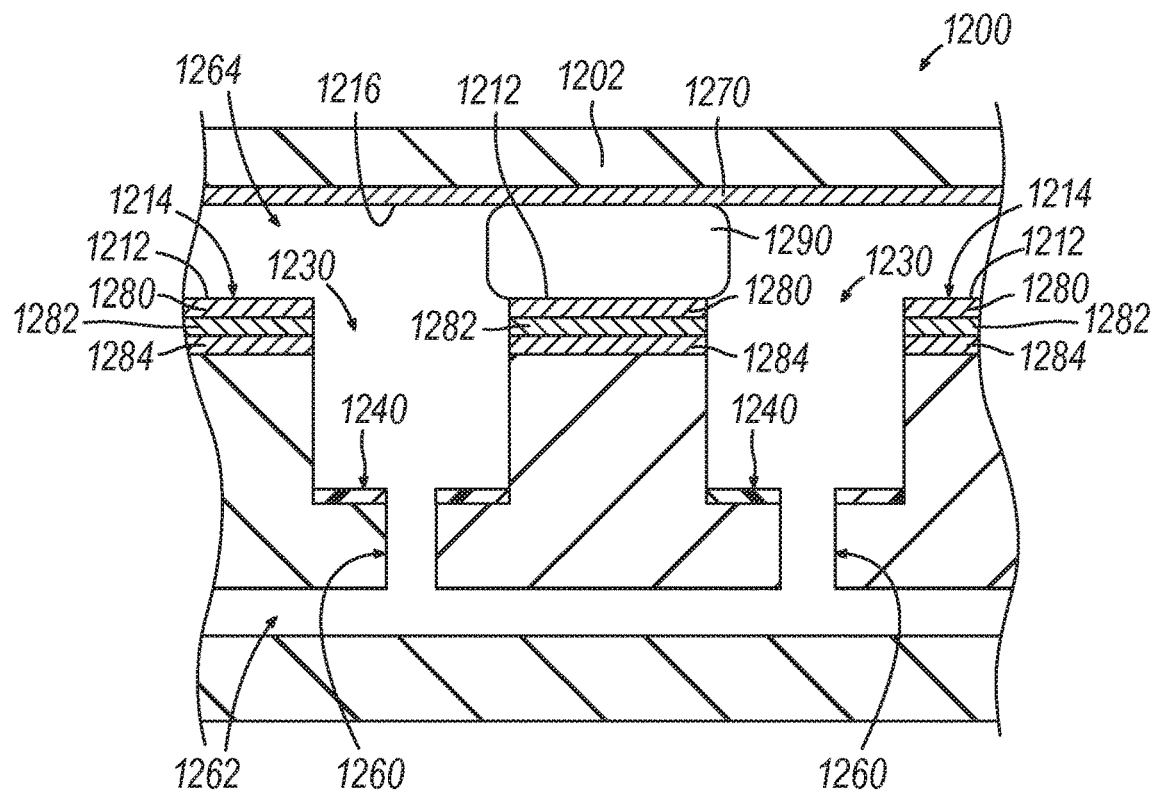
FIG. 16A depicts a block schematic cross-sectional view of a flow cell with a movable barrier positioned between adjacent wells.
Figure 16B:
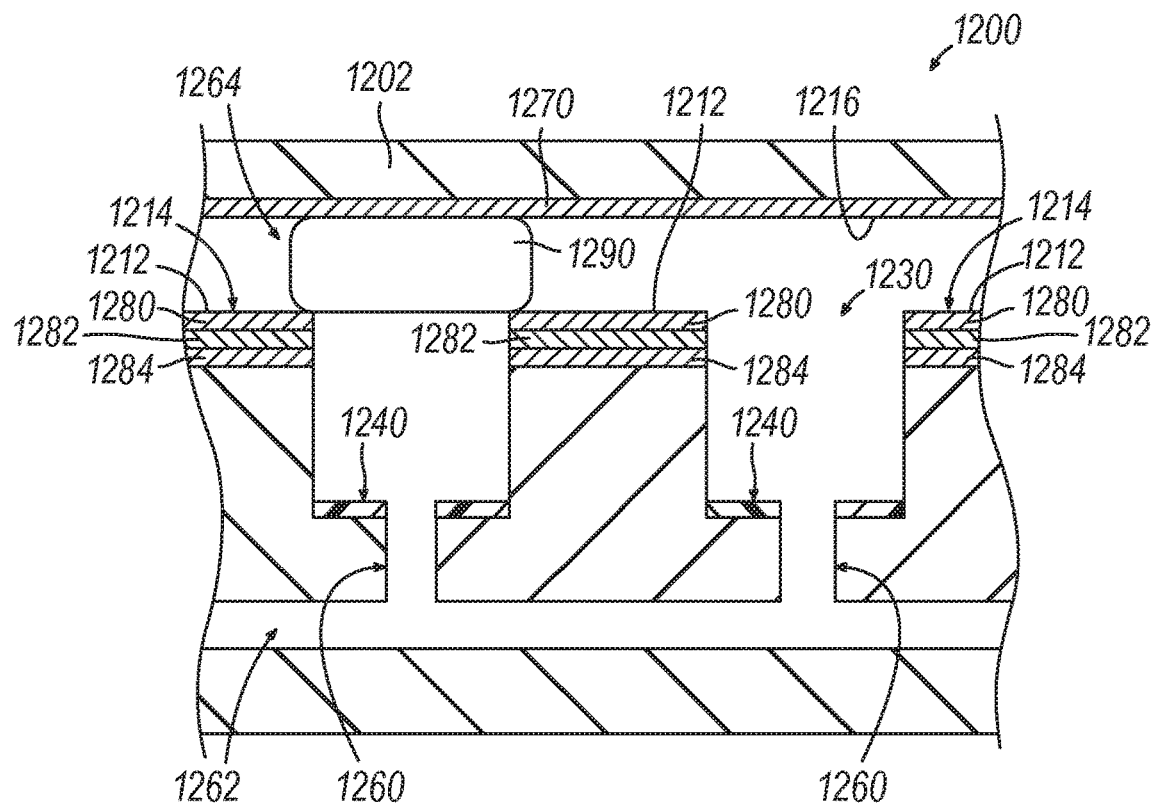
FIG. 16B depicts a block schematic cross-sectional view of the flow cell of FIG. 16A with the movable barrier positioned over one of the wells.

FIGS. 16A-16B show an example of a flow cell 1200 with a barrier member in the form of a droplet 1290 that is operable to selectively transition between two different positions to thereby selectively transition between providing a diffusion prevention barrier (FIG. 16A) and providing a containment barrier (FIG. 16B). In particular, the flow cell 1200 of this example employs digital microfluidics to provide controlled movement of the droplet 1290. The flow cell 1200 of this example includes a ceiling 1202, a lower flow channel 1262, an upper flow channel 1264, and a plurality of wells 1230. The wells 1230 of this example have electrode assemblies 1240 (like other electrode assemblies described herein); and openings 1260 providing a path for fluid communication between the lower flow channel 1262 and the corresponding wells 1230. While not shown in FIGS. 16A-16B, the openings 1260 may include valves (e.g., like valves 780). Similarly, the flow cell 1200 of this example may include any of the other features of the other flow cells 400, 500, 600, 601, 700, 800, 900, 1000, 1100 described herein.

By way of example only, droplet 1290 may comprise oil or any other suitable substance. While only one droplet 1290 is shown in FIGS. 16A-16B, it should be understood that the flow cell 1200 of the present example includes a plurality of droplets 1290 positioned between an upper surface 1216 and a lower surface 1212 of the upper flow channel 1264. The other droplets 1290 may be positioned in the flow cell 1200 either in the interstitial spaces 1214 between wells 1230 (e.g., as shown in FIG. 16A) or over wells 1230 (e.g., as shown in FIG. 16B), depending on the activation state of electrodes in a corresponding electrode layer 1284 as described below. An upper hydrophobic layer 1270 is positioned along the ceiling 1202 of the flow cell 1200 and presents the upper surface 1216. A lower hydrophobic layer 1280 is positioned along the bottom of the flow channel 1264 and presents the lower surface 1212. The droplet 1290 is thus interposed between the hydrophobic layers 1270, 1280.

In some variations, the droplet 1290 is positioned on the lower surface 1212 without necessarily contacting the upper surface 1216. In such variations, the droplet 1290 may extend from the lower surface 1212 toward the upper surface 1216, thereby restricting flow between adjacent wells 1230 without necessarily completely impeding flow between adjacent wells 1230.

In the present example, a dielectric layer 1282 is positioned under the lower hydrophobic layer 1280. An electrode layer 1284 is positioned under the dielectric layer 1282. The electrode layer 1284 includes a patterned array of individually controllable electrode elements (not shown). The electrode elements are isolated from each other. A controller (not shown) is operable to selectively activate and deactivate these electrode elements to provide movement of the droplet 1290 between a first position as shown in FIG. 16A and a second position as shown in FIG. 16B. In particular, the electrode elements selectively apply voltages to the droplets 1290 to provide controlled movement of the droplets 1290. The dielectric layer 1282 may provide build-up of charges and electrical field gradients to thereby provide movement of the droplets 1290. The droplets 1290 thus move based on electrowetting principles. While the droplet 1290 is shown as moving between a first position (FIG. 16A) and a second position (FIG. 16B) in this example, in some variations the droplet 1290 may expand and contract in response to applied electrical field gradients. In some such versions, the droplet 1290 may reside in an interstitial space 1214 when the droplet 1290 is in the contracted state (without covering any wells 1230); and cover one or more wells 1230 when the droplet 1290 is in the expanded state.

When a droplet 1290 is positioned in the interstitial space 1214 between adjacent wells 1230 as shown in FIG. 16A, the droplet 1290 may serve as a physical barrier that prevents diffusion between adjacent wells 1230. When a droplet 1290 is positioned over a well 1230 as shown in FIG. 16B, the droplet 1290 may serve as a cap that physically contains reaction within the capped well 1230. By way of example only, a droplet 1290 may be positioned between wells 1230 as shown in FIG. 16A to prevent diffusion between wells 1230 when liquid is being flowed into a well 1230 via the upper flow channel 1264; and over a well 1230 as shown in FIG. 16B to contain a reaction in a well 1230 (or otherwise prevent diffusion between wells 1230) when liquid is being flowed into the well 1230 via the lower flow channel 1262. Of course, droplet 1290 may also serve as a cap over a corresponding well 1230 even in cases where liquid is not being flowed into the well 1230 via the lower flow channel 1262.

In the example shown in FIGS. 16A-16B, a single droplet 1290 is sized to cover just one single well 1230. In other variations, the droplet 1290 is larger and is sized to cover two or more wells 1230 simultaneously. Droplets 1290 may thus be utilized to selectively cover wells 1230 in groups; rather than just covering single wells 1230 individually. Still other suitable configurations and arrangements will be apparent to those skilled in the art in view of the teachings herein.

The electrode elements in the electrode layer 1284 may be selectively activated by a controller that is directly integrated into the flow cell 1200. By way of example only, such an integrated controller may be incorporated into a CMOS chip. In some such versions, the same CMOS chip or other controller also controls other features of the flow cell 1200 (e.g., the valve 780, the electrode assembly 740, etc.). As another illustrative alternative, the electrode elements in the electrode layer 1284 may be selectively activated by a controller that is directly integrated into a cartridge (e.g., the removable cartridge 200) that receives the flow cell 1200. As still another illustrative alternative, the electrode elements in the electrode layer 1284 may be selectively activated by a controller that is directly integrated into the base instrument 102. Moreover, components of the controller that selectively activates the electrode elements in the electrode layer 1284 may be distributed among two or more of the flow cell 1200, a cartridge that receives the flow cell 1200, or the base instrument 102. Various suitable components and arrangements that may be utilized to provide control of the electrode elements in the electrode layer 1284 will be apparent to those skilled in the art in view of the teachings herein.

F. Electrode Arrangements to Prevent Diffusion

Figure 17:
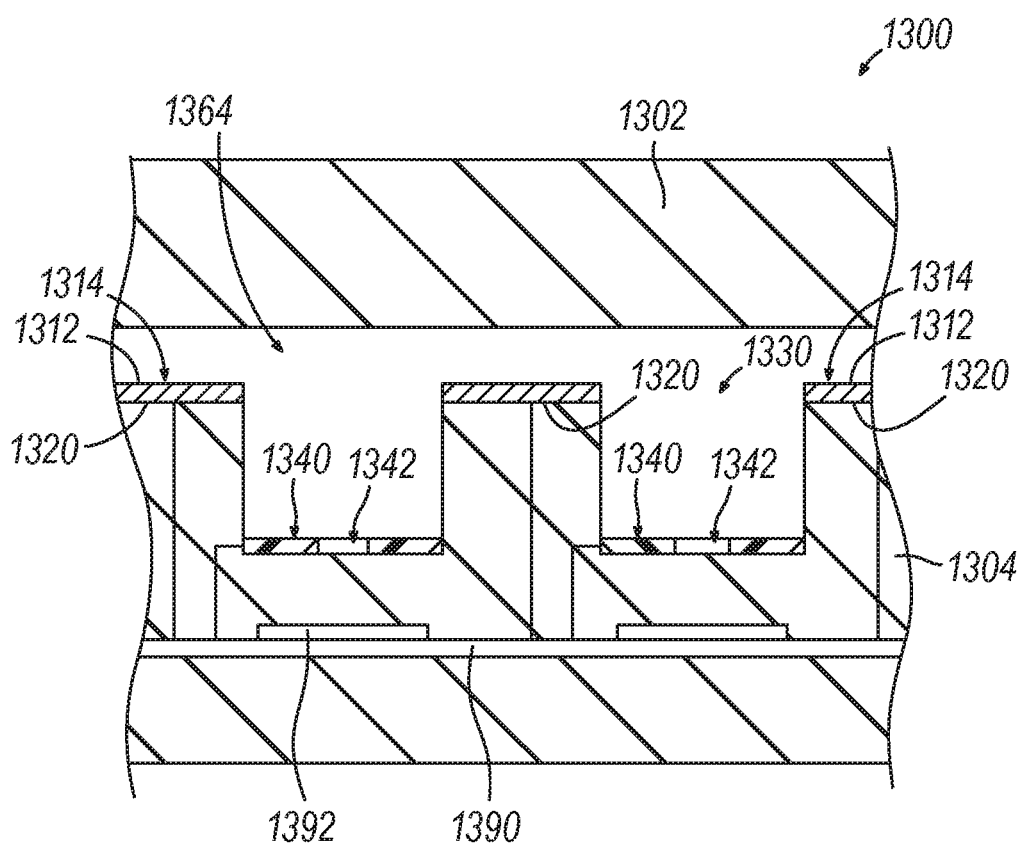
FIG. 17 depicts a block schematic cross-sectional view of another example of a flow cell that may be utilized with the system of FIG. 1.

FIG. 17 shows another example of a flow cell 1300 that may be used to read and write polynucleotides as described herein. The flow cell 1300 of this example includes an upper body portion 1302 and a lower body portion 1304. An upper fluid flow channel 1364 is defined between the upper and lower body portions 1302, 1304 and is operable to receive a flow of fluid (e.g., a fluid containing nucleotide bases, etc.). In the present example, the flow cell 1300 does not include a lower fluid flow channel like other flow cells 600, 601, 700, 800, 900, 1000, 1100 described herein. In some other versions, the flow cell 1300 does include a lower fluid flow channel like other flow cells 600, 601, 700, 800, 900, 1000, 1100 described herein.

The flow cell 1300 of this example further includes a plurality of wells 1330 that are formed as recesses in the bottom surface 1312 of the upper fluid flow channel 1364. These wells 1330 are substantially similar to the wells 630 described above. The flow cell 1300 further defines a plurality of interstitial spaces 1314 between the wells 1330. As noted above, it may be desirable to minimize the size of these interstitial spaces 1314 to thereby maximize the density of wells 1330 within the flow cell 1300. In variations where the flow cell 1300 includes a lower fluid flow channel, the bottom of each well 1330 may include an opening providing a pathway for fluid communication between the well 1330 and the lower fluid flow channel. Such an opening may include a valve that is operable to selectively open or close to thereby selectively permit or prevent fluid communication from the lower fluid flow channel to the corresponding well 1330.

An electrode assembly 1340 is positioned at the bottom of each well 1330. The electrode assembly 1340 may be configured and operable just like the electrode assembly 640 described above. In some versions, the electrode assembly 1340 comprises an active copper element that is operable to drive a redox reaction as part of the process for machine-writing DNA in the well 1330. The flow cell 1300 of this example further includes electrode assemblies 1320 in the interstitial spaces 1314 between the wells 1330, at the lower surface 1312 of the upper fluid flow channel 1364. During the writing process, the electrode assembly 1340 and the electrode assemblies 1320 may be activated simultaneously such that the electrode assemblies 1320 provide generate a current that is reversed in comparison to the current generated by the electrode assemblies 1340. This may effectively sharpen the boundaries of the electrode assembly 1340, which may in turn prevent diffusion between adjacent wells 1130.

As described above, light may be utilized to read machine-written polynucleotides within the wells 1330. In some versions, one or more external light sources is/are used to provide the light. In some other versions, one or more internal light sources is/are used to provide the light. In either case, the light emitted toward the wells 1330 may ultimately reach the polynucleotides within the wells 1330, which may cause fluorophores associated with those polynucleotides to fluoresce. The fluorescence emitted by the fluorophores associated with the polynucleotides may be detected by image sensors 1392 in the lower body portion 1304 of the flow cell 1300. The image sensors 1392 are coupled with a lower integrated circuit layer 1390 that is also positioned in the lower body portion 1304 of the flow cell 1300. In the present example, the image sensors 1392 are in communication with the lower integrated circuit layer 1390 In this context, "in communication" means that the lower integrated circuit layer 1390 is in electrical communication with the image sensors 1392. For instance, the lower integrated circuit layer 1390 may be operable to receive and process signals from the image sensors 1392, with the signals representing images that are picked up by the image sensors 1392. "In communication" in this context may also include the lower integrated circuit layer 1390 providing electrical power to the image sensors 1392.

By way of example only, the lower integrated circuit layer 1390 and image sensors 1392 may be part of a CMOS chip. In some other variations, the lower integrated circuit layer 1390 and image sensors 1392 are integrated into some other component. By way of example only, the lower integrated circuit layer 1390 and/or image sensors 1392 may be integrated into a cartridge (e.g., the removable cartridge 200) that receives the flow cell 1300; may be integrated into the base instrument 102; or may be integrated in some other component.

Each image sensor 1392 is positioned under a corresponding well 1330. Thus, when light source(s) is/are activated to emit light toward the well(s) 1330, the corresponding image sensor(s) 1392 is/are configured to detect fluorescence emitted by fluorophores associated with polynucleotides (e.g., machine-written DNA) contained within the well(s) 1330. The fluorescent light profile detected by image sensors 1392 may be utilized to read the polynucleotides as described herein. As shown in FIG. 17, each electrode assembly 1340 defines an opening 1342 that allows the fluorescence emitted by fluorophores associated with polynucleotides (e.g., machine-written DNA) contained within the well(s) 1330 to pass through the center of the electrode assembly 1340 to thereby reach the corresponding image sensor 1392. To define such an opening, each electrode assembly 1340 may have an annular shape or any other suitable shape.

As is also shown in FIG. 17, the same integrated circuit layer 1390 may be utilized to control the electrode assemblies 1320, 1340 and process image signals captured by the image sensors 1392. In other words, the integrated circuit layer 1390 may be in communication with the electrode assemblies 1320, 1340. Of course, this configuration may be optional. In other versions, different circuit layers or different circuit components may be utilized to control the electrode assemblies 1320, 1340 and/or process image signals captured by the image sensors 1392.

Figure 18:
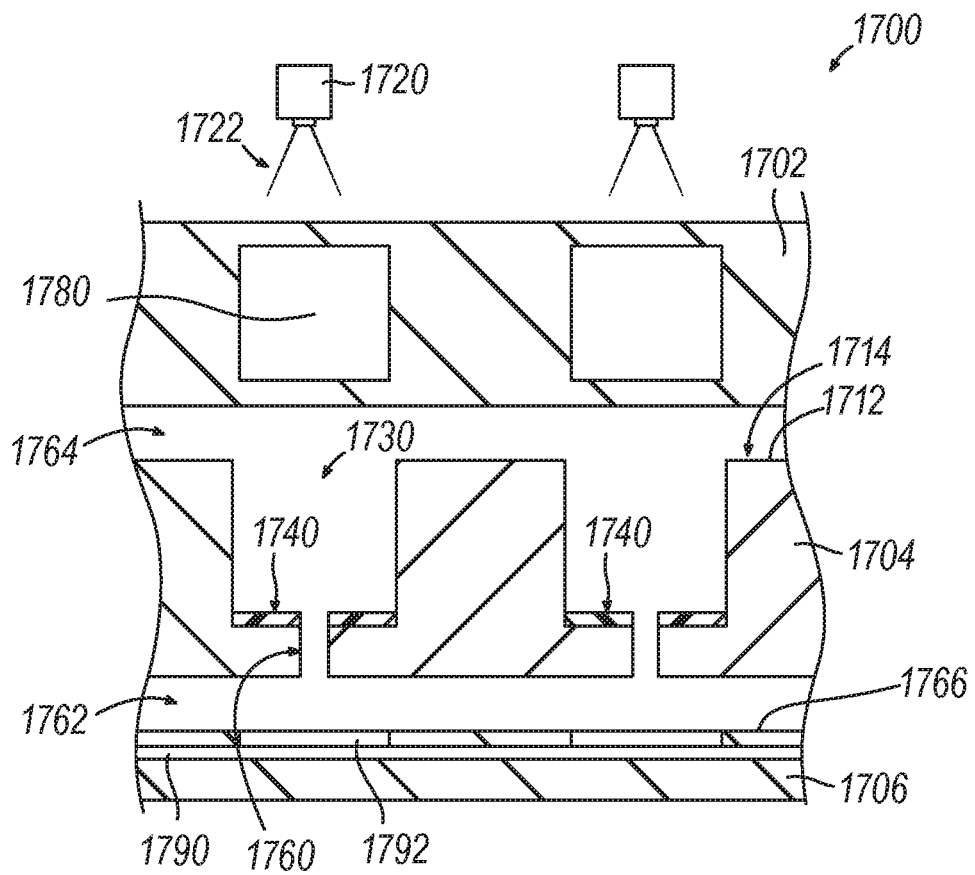
FIG. 18 depicts a block schematic cross-sectional view of an example of a flow cell that may be utilized with the system of FIG. 1.

VIII. Features to Prevent Optical Cross-Talk Between Adjacent Wells of a Flow Cell In order to maximize the amount of data that may be stored in a DNA storage device, it may be beneficial to maximize the number of wells 630 in a flow cell 600, 601 of the DNA storage device. However, increasing the well density in a flow cell 600, 601 may increase the risk of optical cross-talk between wells, particularly when the flow cell comprises an optically transmissive material (e.g., glass, etc.). Such optical cross-talk may compromise the reliability of reading data from, or writing data to, the DNA storage device. It may therefore be desirable to include features that prevent such optical cross-talk. Several illustrative examples of optical cross-talk prevention features are described in greater detail below. While the following examples are provided separately with reference to separate drawings, it should be understood that the features of the following examples may be combined in numerous ways in the same flow cell. Thus, the optical cross-talk prevention features described below should not be viewed as being exclusive of each other A. Optical Elements to Prevent Optical Cross-Talk FIG. 18 shows an example of a flow cell 1700 that may be used to read and write polynucleotides as described herein. The flow cell 1700 of this example includes an upper body portion 1702, a middle body portion 1704, and a lower body portion 1706. An upper fluid flow channel 1764 is defined between the upper and middle body portions 1702, 1704 and is operable to receive a flow of fluid (e.g., a fluid containing nucleotide bases, etc.). A lower fluid flow channel 1762 is defined between the middle and lower body portions 1704, 1706 and is operable to receive a separate flow of fluid (e.g., a fluid containing deblocking/deshielding agents, etc.).

The flow cell 1700 of this example further includes a plurality of wells 1730 that are formed as recesses in the bottom surface 1712 of the upper fluid flow channel 1764. These wells 1730 are substantially similar to the wells 630 described above. The flow cell 1700 further defines a plurality of interstitial spaces 1714 between the wells 1730. As noted above, it may be desirable to minimize the size of these interstitial spaces 1714 to thereby maximize the density of wells 1730 within the flow cell 1700. An electrode assembly 1740 is positioned at the bottom of each well 1730. The electrode assembly 1740 may be configured and operable just like the electrode assembly 640 described above. The bottom of each well 1730 includes an opening 1760 providing a pathway for fluid communication between the well 1730 and the lower fluid flow channel 1762. In some versions, this opening 1760 includes a valve that is operable to selectively open or close to thereby selectively permit or prevent fluid communication from the lower fluid flow channel 1762 to the corresponding well 1730.

As described above, light may be utilized to read machine-written polynucleotides within the wells 1730. To that end, FIG. 18 shows a set of light sources 1720 that are configured to emit light 1722 toward corresponding wells 1730. While each well 1730 has a corresponding light source 1720 in this example, other versions may provide a single light source 1720 that is usable for a plurality of wells 1730. For instance, in such versions, the light source 1720 may be movable relative to the flow cell 1700 to selectively illuminate different wells 1730. Alternatively, the light source 1720 may be fixed in position and the flow cell 1700 may move relative to the light source 1720. In some versions, the light source(s) 1720 is/are external to the flow cell 1700. For instance, the light source(s) 1720 may be integrated into a cartridge (e.g., the removable cartridge 200) that receives the flow cell 1700; may be integrated into the base instrument 102; or may be integrated in some other component. In some other versions the light source(s) 1720 is/are integrated directly into the flow cell 1700 (e.g., within the upper body portion 1702).

The flow cell 1700 of the present example further includes an integrated circuit layer 1790 with a plurality of image sensors 1792. By way of example only, the integrated circuit layer 1790 and image sensors 1792 may be part of a CMOS chip. The integrated circuit layer 1790 and image sensors 1792 are integrated into the lower body portion 1706 in this example, with the image sensors 1792 being positioned at the lower surface 1766 of the lower fluid flow channel 1762. In some other variations, the integrated circuit layer 1790 and image sensors 1792 are integrated into some other component. By way of example only, the integrated circuit layer 1790 and/or image sensors 1792 may be integrated into a cartridge (e.g., the removable cartridge 200) that receives the flow cell 1700; may be integrated into the base instrument 102; or may be integrated in some other component.

Each image sensor 1792 is positioned under a corresponding well 1730. Thus, when light source(s) 1720 is/are activated to emit light 1722 toward the well(s) 1730, the corresponding image sensor(s) 1792 is/are configured to detect fluorescence emitted by fluorophores associated with polynucleotides (e.g., machine-written DNA) contained within the well(s) 1730. The fluorescent light profile detected by image sensors 1792 may be utilized to read the polynucleotides as described herein.

In order to ensure that light 1722 emitted by a light source 1720 only reaches the intended well 1730, the flow cell 1700 of the present example further includes an optical assembly 1780 within the upper body portion 1702 of the flow cell 1700. Each well 1730 has an associated optical assembly 1780 in this example. The optical assembly 1780 may include one or more beam-shaping components. In some versions, the optical assembly 1780 includes an optical waveguide, light pipe, or optical fiber. In addition, or in the alternative, the optical assembly 1780 may include a lens assembly that is configured to focus the intensity of the light 1722 on a lower region of the corresponding well 1730.

In some other variations, the light sources 1720 are positioned underneath the wells 1730, such as below or adjacent to the electrode assembly 1740. Alternatively, the light sources may be positioned at or along the sidewall of each well 1730. As another illustrative variation, the light sources 1720 may be positioned remotely relative to the wells 1730, and the optical assemblies may communicate the light to the wells 1730 via optical fibers, light pipes, or other light-conveying structures.

B. Light Sources to Prevent Optical Cross-Talk

Figure 19:
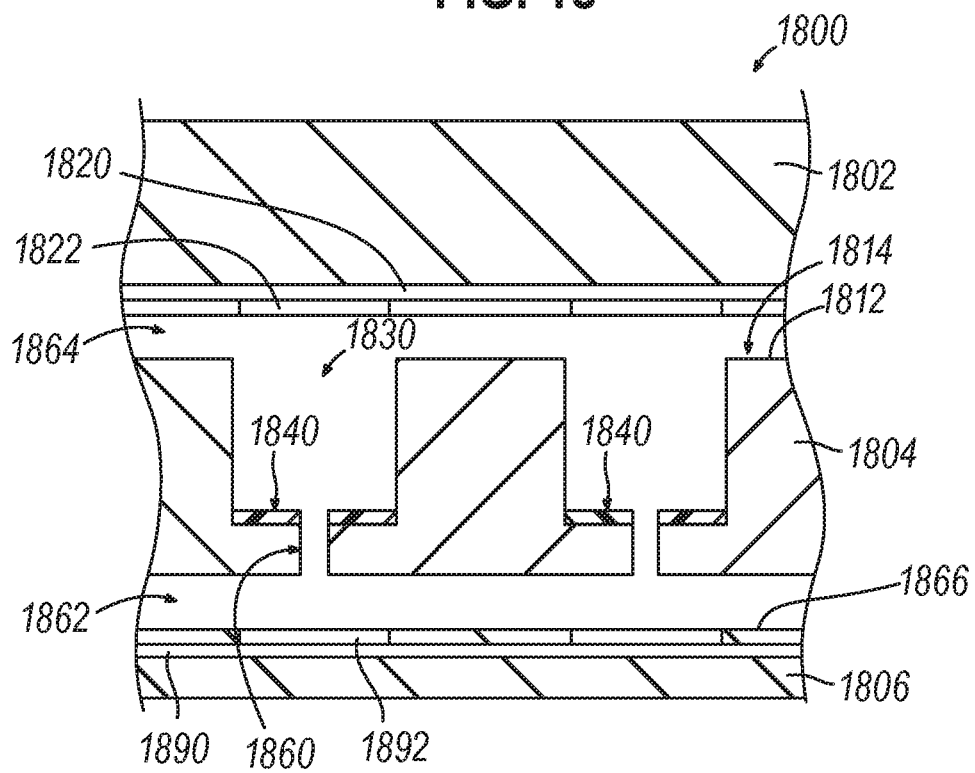
FIG. 19 depicts a block schematic cross-sectional view of another example of a flow cell that may be utilized with the system of FIG. 1.

FIG. 19 shows another example of a flow cell 1800 that may be used to read and write polynucleotides as described herein. The flow cell 1800 of this example includes an upper body portion 1802, a middle body portion 1804, and a lower body portion 1806. An upper fluid flow channel 1864 is defined between the upper and middle body portions 1802, 1804 and is operable to receive a flow of fluid (e.g., a fluid containing nucleotide bases, etc.). A lower fluid flow channel 1862 is defined between the middle and lower body portions 1804, 1806 and is operable to receive a separate flow of fluid (e.g., a fluid containing deblocking/deshielding agents, etc.).

The flow cell 1800 of this example further includes a plurality of wells 1830 that are formed as recesses in the bottom surface 1812 of the upper fluid flow channel 1864. These wells 1830 are substantially similar to the wells 630 described above. The flow cell 1800 further defines a plurality of interstitial spaces 1814 between the wells 1830. As noted above, it may be desirable to minimize the size of these interstitial spaces 1814 to thereby maximize the density of wells 1830 within the flow cell 1800. An electrode assembly 1840 1840 is positioned at the bottom of each well 1830. The electrode assembly 1840 1840 may be configured and operable just like the electrode assembly 640 described above. The bottom of each well 1830 includes an opening 1860 providing a pathway for fluid communication between the well 1830 and the lower fluid flow channel 1862. In some versions, this opening 1860 includes a valve that is operable to selectively open or close to thereby selectively permit or prevent fluid communication from the lower fluid flow channel 1862 to the corresponding well 1830.

As described above, light may be utilized to read machine-written polynucleotides within the wells 1830. To that end, FIG. 19 shows a set of light sources 1822 that are configured to emit light toward corresponding wells 1830. While each well 1830 has a corresponding light source 1822 in this example. The light sources 1822 are all coupled with an upper integrated circuit layer 1820 and are positioned to be flush with the upper surface 1824 of the upper flow channel 1864. The upper integrated circuit layer 1820 is operable to selectively drive the light sources 1822 independently of each other. By way of example only, the upper integrated circuit layer 1820 may include a CMOS chip. By way of further example only, the light sources 1822 may include microscopic light emitting diodes (microLEDs). In some versions, each light source 1822 for each well 1830 consists of a single microLED. In some other versions, each light source 1822 for each well 1830 consists of an array of microLEDs. It should be understood that the use of microLEDs may provide greater precision in the delivery of light to selected wells 1830, thereby minimizing the risk of the emitted light undesirably reaching an adjacent well.

The flow cell 1800 of the present example further includes a lower integrated circuit layer 1890 with a plurality of image sensors 1892. By way of example only, the lower integrated circuit layer 1890 and image sensors 1892 may be part of a CMOS chip. The lower integrated circuit layer 1890 and image sensors 1892 are integrated into the lower body portion 1806 in this example, with the image sensors 1892 being positioned at the lower surface 1866 of the lower fluid flow channel 1862. In some other variations, the lower integrated circuit layer 1890 and image sensors 1892 are integrated into some other component. By way of example only, the lower integrated circuit layer 1890 and/or image sensors 1892 may be integrated into a cartridge (e.g., the removable cartridge 200) that receives the flow cell 1800; may be integrated into the base instrument 102; or may be integrated in some other component.

Each image sensor 1892 is positioned under a corresponding well 1830. Thus, when light source(s) 1822 is/are activated to emit light toward the well(s) 1830, the corresponding image sensor(s) 1892 is/are configured to detect fluorescence emitted by fluorophores associated with polynucleotides (e.g., machine-written DNA) contained within the well(s) 1830. The fluorescent light profile detected by image sensors 1892 may be utilized to read the polynucleotides as described herein.

C. Polarizers to Prevent Optical Cross-Talk

Figure 20:
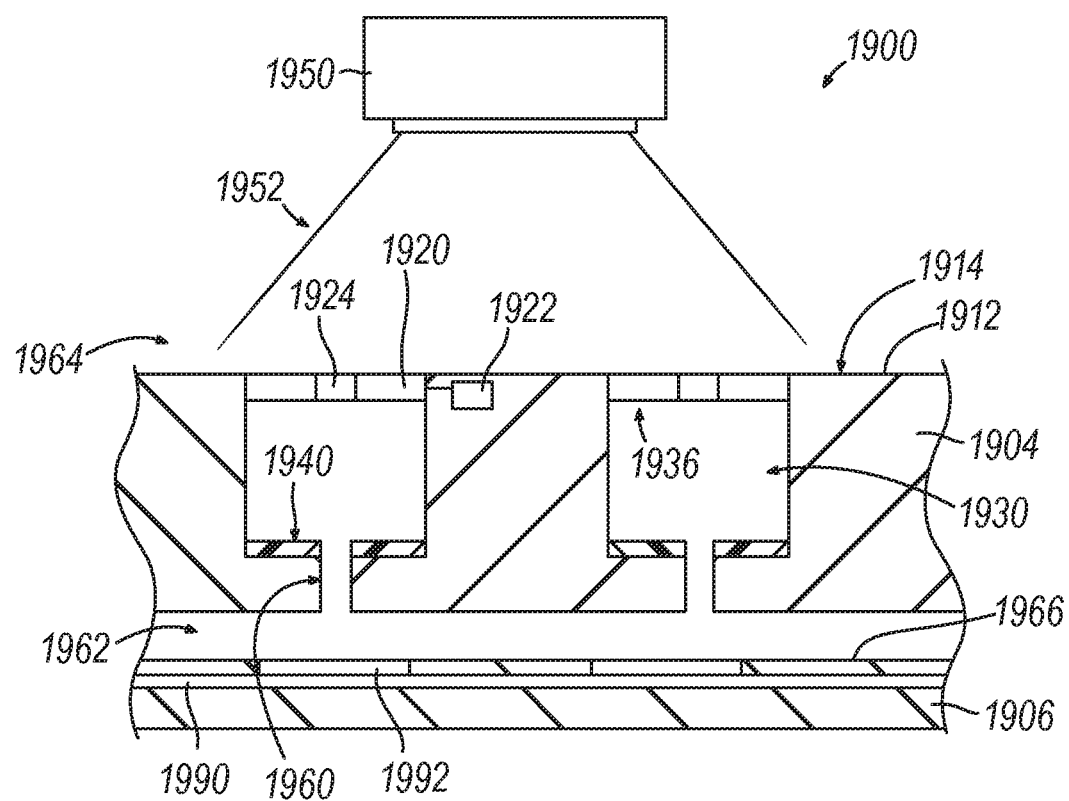
FIG. 20 depicts a block schematic cross-sectional view of another example of a flow cell that may be utilized with the system of FIG. 1.

FIG. 20 shows another example of a flow cell 1900 that may be used to read and write polynucleotides as described herein. The flow cell 1900 of this example includes a first body portion 1904 and a second body portion 1906. An upper fluid flow channel 1964 is defined above the first body portion 1904 and is operable to receive a flow of fluid (e.g., a fluid containing nucleotide bases, etc.). In some versions, an upper body portion (e.g., like the upper body portion 1702, 1802 described above) is positioned over the first body portion 904 to further define the upper fluid flow channel 1964. A lower fluid flow channel 1962 is defined between the first and second body portions 1904, 1906 and is operable to receive a separate flow of fluid (e.g., a fluid containing deblocking/deshielding agents, etc.).

The flow cell 1900 of this example further includes a plurality of wells 1930 that are formed as recesses in the bottom surface 1912 of the upper fluid flow channel 1964. These wells 1930 are substantially similar to the wells 630 described above. The flow cell 1900 further defines a plurality of interstitial spaces 1914 between the wells 1930. As noted above, it may be desirable to minimize the size of these interstitial spaces 1914 to thereby maximize the density of wells 1930 within the flow cell 1900.

A light source 1920 is positioned above the wells 1930 and is configured to emit light 1922 toward the wells 1930. In the example shown in FIG. 20, the light source 1920 is configured to emit a beam of light 1922 that may reach at least two wells 1930. In some versions, the light source 1920 is configured to emit a beam of light 1922 that may reach many more than two wells 1930. In some other versions, each well 1930 has its own dedicated light source 1920, such that the beam of light 1922 from each light source 1920 is intended to only reach one corresponding well 1930.

An electrode assembly 1940 is positioned at the bottom of each well 1930. The electrode assembly 1940 may be configured and operable just like the electrode assembly 640 described above. The bottom of each well 1930 includes an opening 1960 providing a pathway for fluid communication between the well 1930 and the lower fluid flow channel 1962. In some versions, this opening 1960 includes a valve that is operable to selectively open or close to thereby selectively permit or prevent fluid communication from the lower fluid flow channel 1962 to the corresponding well 1930.

As described above, light 1922 from the light source 1920 may be utilized to read machine-written polynucleotides within the wells 1930. The light 1922 emitted toward the wells 1930 may ultimately reach the polynucleotides within the wells 1930, which may cause fluorophores associated with those polynucleotides to fluoresce. The fluorescence emitted by these fluorophores may be detected by image sensors 1992 at the bottom surface 1966 of the lower fluid flow channel 1962. The image sensors 1992 are coupled with a lower integrated circuit layer 1990 that is positioned in the second body portion 1906 of the flow cell 1900. By way of example only, the lower integrated circuit layer 1990 and image sensors 1992 may be part of a CMOS chip. In some other variations, the lower integrated circuit layer 1990 and image sensors 1992 are integrated into some other component. By way of example only, the lower integrated circuit layer 1990 and/or image sensors 1992 may be integrated into a cartridge (e.g., the removable cartridge 200) that receives the flow cell 1900; may be integrated into the base instrument 102; or may be integrated in some other component.

Each image sensor 1992 is positioned under a corresponding well 1930. Thus, when light source(s) is/are activated to emit light toward the well(s) 1930, the corresponding image sensor(s) 1992 is/are configured to detect fluorescence emitted by fluorophores associated with machine-written DNA contained within the well(s) 1930. The fluorescent light profile detected by image sensors 1992 may be utilized to read the polynucleotides as described herein.

When wells 1930 are densely packed together in a flow cell 1900, such that the interstitial spaces 1914 are very small, and one light source 1950 is utilized to illuminate two or more adjacent wells 1930, it may be difficult to selectively illuminate just one well 1930 without simultaneously illuminating an adjacent well 1930. Similarly, it may be difficult to illuminate two non-adjacent wells 1930 simultaneously with the same light source 1950 without also simultaneously illuminating any wells 1930 that are adjacent to the targeted wells 1930. The selective illumination of particular wells 1930 with a single light source 1950 that is capable of illuminating two or more wells 1930 may be desirable in cases where it is desired to only read polynucleotides that have been written in the targeted wells 1930.

To provide enhanced control of illumination of wells 1930 with a single light source 1950 (or at least a light source 1950 that is operable to illuminate two or more wells 1930 simultaneously), the flow cell 1900 of the present example includes electrically activated polarizers 1920 located in the upper regions 1936 of the wells 1930. Each polarizer 1920 has a corresponding activation controller 1922 that is operable to selectively activate the polarizer 1920 to transition between a polarizing state and a non-polarizing state (e.g., by selectively applying a voltage to the polarizer 1920 or removing the voltage from the polarizer 1920). When the polarizer 1920 is activated, the polarizer may provide an optical barrier between the light source 1950 and the well 1930 associated with the polarizer 1920. When the polarizer 1920 is not activated, the polarizer 1920 may allow light 1952 from the light source 1950 to reach the well 1930. Thus, when it is desired to allow the light 1952 to reach some targeted wells 1930 without reaching other, non-targeted wells 1930, the polarizers 1920 of the targeted wells 1930 may be left in a non-activated state (to thereby allow light 1952 to pass through the polarizers 1920 of the targeted wells (1930)); while the polarizers 1920 of the non-targeted wells 1930 may be in an activated state (to thereby prevent light 1952 from passing through the polarizers 1920 of the non-targeted wells (1930)). In other words, the polarizers 1920 may be utilized to prevent light 1952 from reaching wells 930 that are not intended to receive light 1952.

Also in the present example, each polarizer 1920 has a respective opening 1924 that is configured to allow fluid to flow from the upper fluid flow channel 1964 into the well 1930. While this opening 1924 is sized to accommodate the flow of fluid therethrough, the opening 1924 is still small enough to not meaningfully affect the ability of the polarizer 1920 to effectively block light 1952 from the light source 1950 when the polarizer 1920 is activated. In other words, even with the opening 1924, the polarizer 1920 may substantially permit fluid communication through the polarizer 1920 while substantially preventing optical communication through the polarizer 1920. Some other versions of the polarizers 1920 may lack openings 1924. For instance, some such versions may be utilized in variations of the flow cell 1900 that lack the upper fluid flow channel 1964. Such variations of the flow cell 1900 may provide fluid communication to the wells 1930 only via the lower fluid flow channel 1962 (or through some other route). Some other variations of the flow cell 1900, where the polarizers 1920 lack openings 1924, may provide alternative paths for fluid flow from the upper fluid flow channel 1964 into the wells 1930. For instance, the first body portion 1904 may define additional flow paths for each well 930, fluidically coupling the upper fluid flow channel 1964 with each well 1930 via the sidewall of the well 1930 (i.e., to a point under the polarizer 1920).

D. Methods to Prevent Optical Cross-Talk or Otherwise Provide Efficiency

In addition to employing any of the various different hardware configurations described above to prevent optical cross-talk between adjacent wells of a flow cell, various techniques may be utilized to prevent optical cross-talk between adjacent wells of a flow cell or otherwise provide efficiency in reading and/or writing machine-written DNA. Examples of such techniques are described in greater detail below. It should be understood that the below described techniques may be utilized in any of the flow cells 600, 601, 1700, 1800, 1900 described herein or in any other suitable flow cell.

FIG. 21 shows an example of a method that employs a fragmenting approach to writing data, by showing a preference to leaving pixels or wells adjacent to a written pixel or well empty. It should be understood that data may also be read at a faster speed it is known that the adjacent pixels or wells are empty; and the read speed may be reduced if it is known that the adjacent pixels or wells have some contents. Leaving adjacent pixels or wells empty may also enable a more rapid transition from a read-action on a pixel or well to a write-action on an adjacent pixel or well.

The process depicted in FIG. 21 begins with identifying 2200 unused wells within a flow cell. For each unused well that is identified, the process includes determining 2202 whether the unused well is adjacent to a used well. If the identified unused well is in fact adjacent to a used well, then the process continues with evaluating 2204 the unused wells to find a well that is not adjacent to a used well. When the process identifies an unused well that is not adjacent to a used well, the process proceeds with placing 2206 that unused well in a first subset. The process then includes determining 2208 whether there are sufficient unused wells form a first subset. This determination may be based on the amount of data that needs to be stored and/or other factors. If there are not yet enough unused wells in the first subset, then the process continues evaluating 2204 the unused wells to find another well that is not adjacent to a used well. The above process may be repeated until enough unused wells are placed in the first subset.

Once the first subset of unused wells is complete, the process proceeds to activating 2210 the electrode assemblies for those wells of the first subset to generate machine-written polynucleotides in those wells. In some scenarios, the process ends at this stage. It should also be understood that it may be unnecessary to activate any barrier features, such as those described above to prevent cross-talk, before activating 2210 the electrode assemblies to generate machine-written polynucleotides in the wells of the first subset. In particular, since the adjacent wells do not contain any machine-written DNA at this stage of the process, there is no need for concern with cross-talk in those adjacent wells.

In some other scenarios, the process then proceeds to identifying 2212 more unused wells. For each unused well, the process then determines 2214 whether the unused well is adjacent to a used well. If the identified unused well is not adjacent to a used well, then the process continues evaluating 2216 the unused wells to find a well that is adjacent to a used well. When the process identifies an unused well that is adjacent to a used well, the process proceeds to placing 2218 that unused well in a second subset. Then, a barrier feature associated with that unused well in the second subset is activated 2220 before initiating a write procedure in that unused well. With the barrier feature activated, the electrode assembly for that well is then activated 2222 to generate machine-written polynucleotides in that well. In this example, only one unused well was placed in the second subset. In some other versions, more than one unused well may be placed in the second subset, such that the process may include a determination of whether the second subset is complete (before moving on to activating 2220 one or more barrier features).

In some scenarios, a charge or "charge tag" may be added to a nucleotide or to an enzyme to reduce the power demand on electrode assemblies 640, 1740, 1840 1840, 1940 during a writing process. Reducing the demand on electrode assemblies 640, 1740, 1840 1840, 1940 during a writing process may allow the form factor of electrode assemblies 640, 1740, 1840 1840, 1940 to be reduced. Reducing the demand on electrode assemblies 640, 1740, 1840 1840, 1940 during a writing process may also reduce the electrical power load on the circuit and associated components that drive the electrode assemblies 640, 1740, 1840 1840, 1940. Adding charge tags to a nucleotide or to an enzyme may also allow for selective "recruitment" and "de-recruitment" via selective polarity of the nucleotides and/or enzymes to a given well 630, 1730, 1830, 1930. Such recruitment and de-recruitment may include concentrating the desired nucleotide or substrate-enzyme complex by electrostatic attraction ("recruitment"); or doing the reverse by repulsion ("de-recruitment").

IX. Miscellaneous

All of the references, including patents, patent applications, and articles, are explicitly incorporated by reference herein in their entirety.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

As used herein, an element or step recited in the singular and proceeded with the word "a" or "an" should be understood as not excluding plural of said elements or steps, unless such exclusion is explicitly stated. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this Specification are used to describe and account for small fluctuations, such as due to variations in processing. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

There may be many other ways to implement the subject technology. Various functions and elements described herein may be partitioned differently from those shown without departing from the scope of the subject technology. Various modifications to these implementations may be readily apparent to those skilled in the art, and generic principles defined herein may be applied to other implementations. Thus, many changes and modifications may be made to the subject technology, by one having ordinary skill in the art, without departing from the scope of the subject technology. For instance, different numbers of a given module or unit may be employed, a different type or types of a given module or unit may be employed, a given module or unit may be added, or a given module or unit may be omitted.

Underlined and/or italicized headings and subheadings are used for convenience only, do not limit the subject technology, and are not referred to in connection with the interpretation of the description of the subject technology. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. An apparatus, comprising:
(a) a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth;
(b) a plurality of electrodes, each electrode of the plurality of electrodes being positioned in a corresponding well of the plurality of wells, the plurality of electrodes to effect writing of polynucleotides in the corresponding wells of the plurality of wells; and
(c) a temperature gradient generator, the temperature gradient generator to provide a temperature profile that varies across the depth of each well of the plurality of wells.

2. The apparatus of claim 1, further comprising an imaging assembly to capture images indicative of one or more nucleotides in a polynucleotide.

3. The apparatus of claim 1, the temperature gradient generator to provide a relatively higher temperature in a bottom region of each well of the plurality of wells and a relatively lower temperature in a top region of each well of the plurality of wells.

4. A method comprising:
flowing fluid through a flow cell, the fluid containing nucleotides, the flow cell comprising a flow cell body defining one or more flow channels, each flow channel of the one or more flow channels to receive a flow of fluid, each flow channel of the one or more flow channels having:
(i) a floor,
(ii) a plurality of wells defined as recesses in the floor, each well of the plurality of wells being fluidically coupled with the corresponding flow channel of the one or more flow channels, the floor of the flow channel of the one or more flow channels defining interstitial surfaces between adjacent wells of the plurality of wells, and
(iii) a plurality of barrier features positioned above the plurality of wells or in the plurality of wells, the plurality of barrier features to reduce optical cross-talk between the plurality of wells;
determining a first subset of the plurality of wells that are unused, and that are not adjacent to a used well of the plurality of wells;
activating electrode assemblies at bottom regions of each well of the first subset to generate machine-written polynucleotides within each well of the first subset, the machine-written polynucleotides within each well of the first subset representing stored data, while leaving the plurality of barrier features deactivated;
determining a second subset of the plurality of wells that are unused, but that are adjacent to a used well of the plurality of wells; and
activating electrode assemblies at bottom regions of each well of the second subset to generate machine-written polynucleotides within each well of the second subset, the machine-written polynucleotides the machine-written polynucleotides within each well of the second subset representing stored data, after activating the barrier features to reduce optical cross-talk between adjacent wells of the plurality of wells.

5. The method of claim 4, further comprising:
receiving a request for stored data;
determining a set of target wells from the plurality of wells in which the stored data is represented by machine-written polynucleotides;
determining whether each well of the set of target wells is adjacent to any used wells of the plurality of wells; and
where a target well of the set of target wells is adjacent to any used well, activating an integrated circuit to detect fluorescence emitted from a fluorophore of a machine-written polynucleotide and read the stored data from the target well of the set of target wells that is adjacent to a used well, after activating the barrier features to reduce optical cross-talk with the adjacent wells of the plurality of wells.

6. The method of claim 5, further comprising:
where the target well is adjacent to any used well, performing a cross-talk quality control check on the read stored data; and
where the cross-talk quality control check verifies that that read stored data is not corrupted, providing the read stored data to a requesting device.

7. The method of claim 4, further comprising:
receiving a request for stored data;
determining a set of target wells from the plurality of wells in which the stored data is represented by machine-written polynucleotides;
determining whether each well of the set of target wells is adjacent to any used wells of the plurality of wells; and
where a target well of the set of target wells is not adjacent to any used well, activating an integrated circuit to detect fluorescence of emitted from a fluorophore of a machine-written polynucleotide and read the stored data from the target well of the set of target wells that is not adjacent to a used well, while leaving the barrier features deactivated.

8. The method of claim 5, further comprising, where the target well is not adjacent to any used well of the plurality of wells, providing the read stored data to a requesting device without performing a cross talk quality control check on the read stored data.

9. The apparatus of claim 2, the temperature gradient generator to provide a relatively higher temperature in a bottom region of each well of the plurality of wells and a relatively lower temperature in a top region of each well of the plurality of wells.

10. The method of claim 5, further comprising:
receiving a request for stored data;
determining a set of target wells from the plurality of wells in which the stored data is represented by machine-written polynucleotides;
determining whether each well of the set of target wells is adjacent to any used wells of the plurality of wells; and
where a target well of the set of target wells is not adjacent to any used well, activating an integrated circuit to detect fluorescence of emitted from a fluorophore of a machine-written polynucleotide and read the stored data from the target well of the set of target wells that is not adjacent to a used well, while leaving the barrier features deactivated.

11. The method of claim 6, further comprising:
receiving a request for stored data;
determining a set of target wells from the plurality of wells in which the stored data is represented by machine-written polynucleotides;
determining whether each well of the set of target wells is adjacent to any used wells of the plurality of wells; and
where a target well of the set of target wells is not adjacent to any used well, activating an integrated circuit to detect fluorescence of emitted from a fluorophore of a machine-written polynucleotide and read the stored data from the target well of the set of target wells that is not adjacent to a used well, while leaving the barrier features deactivated.

12. The method of claim 6, further comprising, where the target well is not adjacent to any used well of the plurality of wells, providing the read stored data to a requesting device without performing a cross talk quality control check on the read stored data.

13. The method of claim 7, further comprising, where the target well is not adjacent to any used well of the plurality of wells, providing the read stored data to a requesting device without performing a cross talk quality control check on the read stored data.

* * * * *